Figure 1:
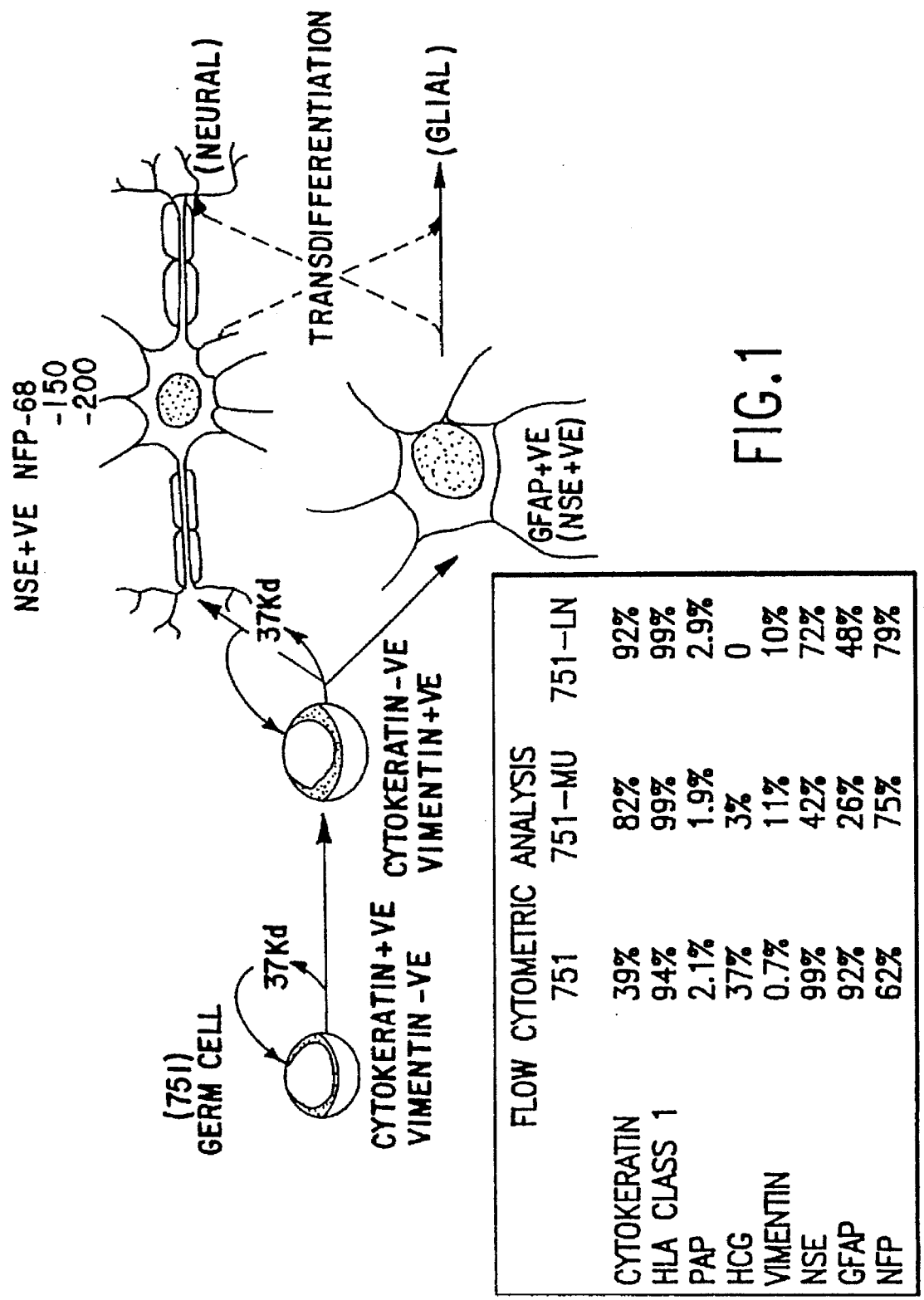

United States Patent [19]

Lawman et al.

[11] Patent Number: 5,650,299

[45] Date of Patent: Jul. 22, 1997

[54] CELLS PRODUCING STEM CELL PROLIFERATION FACTOR

[75] Inventors: Michael J. P. Lawman; Patricia D. Lawman, both of Orlando; Nancy D. Denslow, Gainesville, all of Fla.

[73] Assignee: The University of Florida, Gainesville, Fla.

[21] Appl. No.: 319,165

[22] Filed: Oct. 6, 1994

Related U.S. Application Data

[63] Continuation-in-part of Ser. No. 132,994, Oct. 6, 1993, abandoned.

[51] Int. Cl.$^6$ .............................. C12P 21/02; C12N 5/06; C12N 5/08
[52] U.S. Cl. ..................... 435/70.7; 435/71.1; 435/354; 435/372; 435/325; 530/350; 530/351
[58] Field of Search ................. 435/240.2, 70.1, 435/71.1; 530/350, 351

[56] References Cited

FOREIGN PATENT DOCUMENTS

WO93/20197  10/1993  WIPO.
WO95/09912   4/1995  WIPO.

OTHER PUBLICATIONS

Bagwell et al., "Regulation of Tumor Growth by Antibody to a Novel Autocrine Growth Factor," *Surg. Formum.* 43(0):609–613, Oct. 11–16, 1992.

Bruno et al., "Further Examination of the Effects of Recombinant Cytokines on the Proliferation of Human Megakaryocyte Progenitor Cells," *Blood*, 77(11):2339–2346, Jun. 1991.

Cicuttini et al., "The Effect of Recombinant Stem Cell Factor (SCF) on Purified CD34–Positive Human Umbilical Cord Blood Progenitor Cells," *Growth Factors*, 6(1):31–39, 1992.

Goding, "Monoclonal Antibodies: Principles and Practice", 2nd Edition, pp. 59–103 Academic Press, 1986.

Litzow et al., "Proliferative Responses to Interleukin–3 and Granulocyte Colony–Stimulating Factor Distinguish a Minor Subpopulation of CD34–Positive Marrow Progenitors that do not Express CD33 and a Novel Antigen, 7B9," *Blood*, 77(11):2354–2359, Jun. 1991.

McNiece et al., "Recombinant Human Cell Factor Synergies with GM–CSF, G–CSF, IL–3 and epo to Simulate Human Progenitor Cells of the Myeloid and Erythroid Lineages," *Exp. Hematol.*, 19(3):226–231, Mar. 1991.

Moore et al., "Cytokine Networks Involved in the Regulation of Haemopoietic Stem Cell Proliferation and Differentiation," *Ciba Foundation Symposium*, 143, 43–61, 1990.

Strauss et al., "Initiation in DNA Synthesis by Colony–Stimulating Factors in Subsets of Human CD34 Positive Marrow Cells," *Exp. Hematol*, 19(8):734–741, 1991.

Thomas et al., "In Vitro Effects of Recombinant Hemopoietic Growth Factors on Progenitor Cells from Patients with Myelodysplastic Syndromes," *Leuk. Res.*, 15(1):29–36, 1991.

Waldmann, "Monoclonal Antibodies in Diagnosis and Therapy," *Science*, 252:1657–1662, Jun. 1991.

*Primary Examiner*—Stephen Walsh
*Assistant Examiner*—Sally P. Teng
*Attorney, Agent, or Firm*—Arnold, White & Durkee

[57] ABSTRACT

The present invention is directed to an autocrine growth factor. In particular, it relates to the production, purification and uses of stem cell proliferation factor (SCPF). In various cell lines, the protein of the invention exists in two forms, a soluble form and a membrane bound form which is detectable on the surface of a small percentage of human bone marrow cells and stimulates the proliferation of these cells. Therefore, SCPF may have a wide range of applications including but not limited to augmenting the growth of hematopoietic stem cells. Further, removal of the protein by an antibody may be useful in controlling tumor cell growth.

4 Claims, 23 Drawing Sheets

CELLS PRODUCING STEM CELL PROLIFERATION FACTOR

This application is a continuation-in-part of application Ser. No. 08/132,994, filed Oct. 6, 1993, now abandoned.

1. INTRODUCTION

The present invention is directed to an autocrine growth factor isolated from a germ cell tumor line and a human CD34+ cell line. In particular, it relates to the production, purification and uses of stem cell proliferation factor (SCPF). In various cell lines, the protein of the invention may exist in two forms, a soluble form and a membrane bound form which is detectable on the surface of a small percentage of human bone marrow cells and stimulates the proliferation of these cells. Therefore, SCPF may have a wide range of applications including but not limited to augmenting the growth of hematopoietic stem cells. Further, removal of the protein by an antibody may be useful in controlling tumor cell growth.

2. BACKGROUND OF THE INVENTION

Growth factors have been described that exert their stimulatory effects on the cells that produce them in an autocrine fashion. The same factors may display similar activities on other target cells. However, it has not been described in the literature that tumor cells obtained from the nervous system produce factors that regulate the growth of cells of the hematopoietic system.

2.1. Germ Cell Tumors

Germ cell tumors of the central nervous system are rare, comprising less than 3% of pediatric solid tumors. These tumors arise most commonly in the pineal gland and hypothalamus, though they have been described in the thalamus and basal ganglia. Histologically, these tumors are most commonly found to be germinomas. Less common sub-types include choriocarcinoma, embryonal germ cell tumor, and mixed germ cell tumor. These types of tumor in general have a worse prognosis.

The treatment of these tumors is multimodal, with surgery and radiation therapy for germinomas, with intensive platinum-based chemotherapy protocols and autologous bone marrow transplantation playing a significant role for patients with non-germinomatous germ cell tumors, metastatic disease, or recurrent disease. Metastatic spread via ventricular shunts has been reported and may occur anywhere along the tract of the shunt. Metastatic deposits in the neck and the lung have been reported, but most commonly these deposits are associated with ventricular peritoneal shunts and large peritoneal implants. Cell lines cultured from intracranial germ cell tumors are uncommonly reported, though several cell lines have been derived from germ cell tumors of extra-neural origin. Continuous in vitro cell lines have been derived from rat carcinomas. These cell lines have proven very valuable in the study of differentiation of primitive pluripotent cells.

2.2. Hematopoietic Cells and Growth Factors

In human medicine, the ability to initiate and regulate hematopoiesis is of great importance (McCune et al., 1988, Science 241:1632). A variety of diseases and immune disorders, including malignancies, appear to be related to disruptions within the lympho-hematopoietic system. Many of these disorders could be alleviated and/or cured by repopulating the hematopoietic system with progenitor cells, which when triggered to differentiate would overcome the patient's deficiency. In humans, a current replacement therapy is bone marrow transplantation. Apart from the use of bone marrow transplantation in the treatment of leukemia, it is now frequently being used in other neoplasia (Epstein and Slease, 1985, Surg. Ann. 17:125). This type of therapy, however, is both painful (for donor and recipient) because of involvement of invasive procedures and can offer severe complications to the recipient, particularly when the graft is allogeneic and Graft Versus Host Disease (GVHD) results. Therefore, the risk of GVHD restricts the use of bone marrow transplantation to patients with otherwise fatal diseases. A potentially more exciting alternative therapy for hematopoietic disorders is the treatment of patients with any one or combination of colony stimulating factors (Dexter, 1987, J. Cell Sci. 88:1).

The process of blood cell formation, by which a small number of self-renewing stem cells give rise to lineage specific progenitor cells that subsequently undergo proliferation and differentiation to produce the mature circulating blood cells is under the control of specific hormones. These hormones are collectively known as colony stimulating factors (CSFs) (Metcalf, 1985, Science 229:16; Dexter, 1987, J. Cell Sci. 88:1; Golde and Gasson, 1988, Scientific American, July: 62; Tabbara and Robinson, 1991, Anti-Cancer Res. 11:81; Ogawa, 1989, Environ. Health Presp. 80:199; Dexter, 1989, Br. Med. Bull. 45:337). With the advent of recombinant DNA technology, a number of these CSFs have now been cloned and expressed (Souza et al., 1986, Science 232:61; Gough et al., 1984, Nature 309:763; Yokota et al., 1984, Proc. Natl. Acad. Sci. U.S.A. 81:1070; Kawasaki et al., 1985, Science 230:291). These recombinant CSFs are now available and extensive studies into their therapeutic potential have begun. Their potential uses in medicine are far-reaching and include such areas as blood transfusions, bone marrow transplantation, correcting immunosuppressive disorders, cancer therapy, wound healing, and activation of the immune response. (Golde and Gasson, 1988, Scientific American, July: 62). Apart from inducing proliferation and differentiation of hematopoietic progenitor cells, CSFs have also been shown to activate a number of functions of mature blood cells (Stanley et al., 1976, J. Exp. Med. 143:631; Schrader et al., 1981, Proc. Natl. Acad. Sci. U.S.A. 78:323; Moore et al., 1980, J. Immunol. 125:1302; Kurland et al., 1979, Proc. Natl. Acad. Sci. U.S.A. 76:2326; Handman and Burgess, 1979, J. Immunol. 122:1134; Vadas et al., 1983, Blood 61:1232; Vadas et al., 1983, J. Immunol. 130:795), including influencing the migration of mature hematopoietic cells (Weibart et al., 1986, J. Immunol. 137:3584).

3. SUMMARY OF THE INVENTION

The present invention relates to stem cell proliferation factor (SCPF), its use in stimulating growth of various stem cell populations including hematopoietic stem cells, and a method for identifying other growth factors or cytokines produced by germ cell tumors or other cell lines. SCPF is a family of novel autocrine growth factors which stimulate the proliferation of human bone marrow stem cells. SCPF is expressed by a murine cell line designated 751 as a secreted form of 32,000 daltons and membrane bound form of 37,000 daltons molecular weight. SCPF is also expressed by a cell line designated ML-1 at a molecular weight of 23,000 daltons. SCPF stimulates proliferation and growth of cell lines that produce it as well as CD34$^+$ human bone marrow stem cells.

The invention is based, in part, on the Applicants' discovery that murine cell line 751 releases an autocrine growth factor into the culture medium. Polyclonal rabbit antibody (SAM.1) generated against the purified 32 kDa protein recognizes both a 32 kDa secreted product and a 37 kDa cell bound protein produced by 751 cells and a 23 kDa protein produced by ML-1 cells. This antibody is also capable of identifying a cell population in human bone marrow, reacting with less than 2.6% of normal (adherent-depleted) bone marrow cells. This SCPF$^+$ bone marrow cell population co-expresses the stem cell marker CD34. As shown in the working examples described herein, the biological activity of SCPF is distinct from any of the known bone marrow colony stimulating factors (CSF) including GM-CSF, G-CSF, M-CSF and IL-3. In addition, antibodies specific for GM-CSF, G-CSF, M-CSF and IL-3 do not inhibit the biologic activities of SCPF. Further, SCPF is also distinct from the ligand for the c-kit oncogene product (SCF) as anti-SCPF antibody does not neutralize SCF function.

The invention is described by way of examples in which SCPF is identified as an autocrine growth factor produced by certain cell lines, such as those described herein, and the biochemical and biological properties of the factor are characterized. A wide variety of uses for these novel proteins are encompassed by the invention described herein.

4. BRIEF DESCRIPTION OF THE DRAWINGS

FIG. 1. Phenotype characterization by Flow Cytometric Analysis. The 751 cell line was stained with antibodies directed against antigen markers specific for cytoskeletal structures for non-neuro-ectodermal germ cells (anti-PAP, anti-HCG), and germ cells of neural origin (anti-cytokeratin, vimentin, NSE, GFAP, and NFP). Anti-HLA class I was used as a control. The pattern of staining, shown in the box, is indicative of this cell line being primitive neuro-ectodermal cell capable of differentiation into cells of neuronal or glial lineages.

Figure 2:
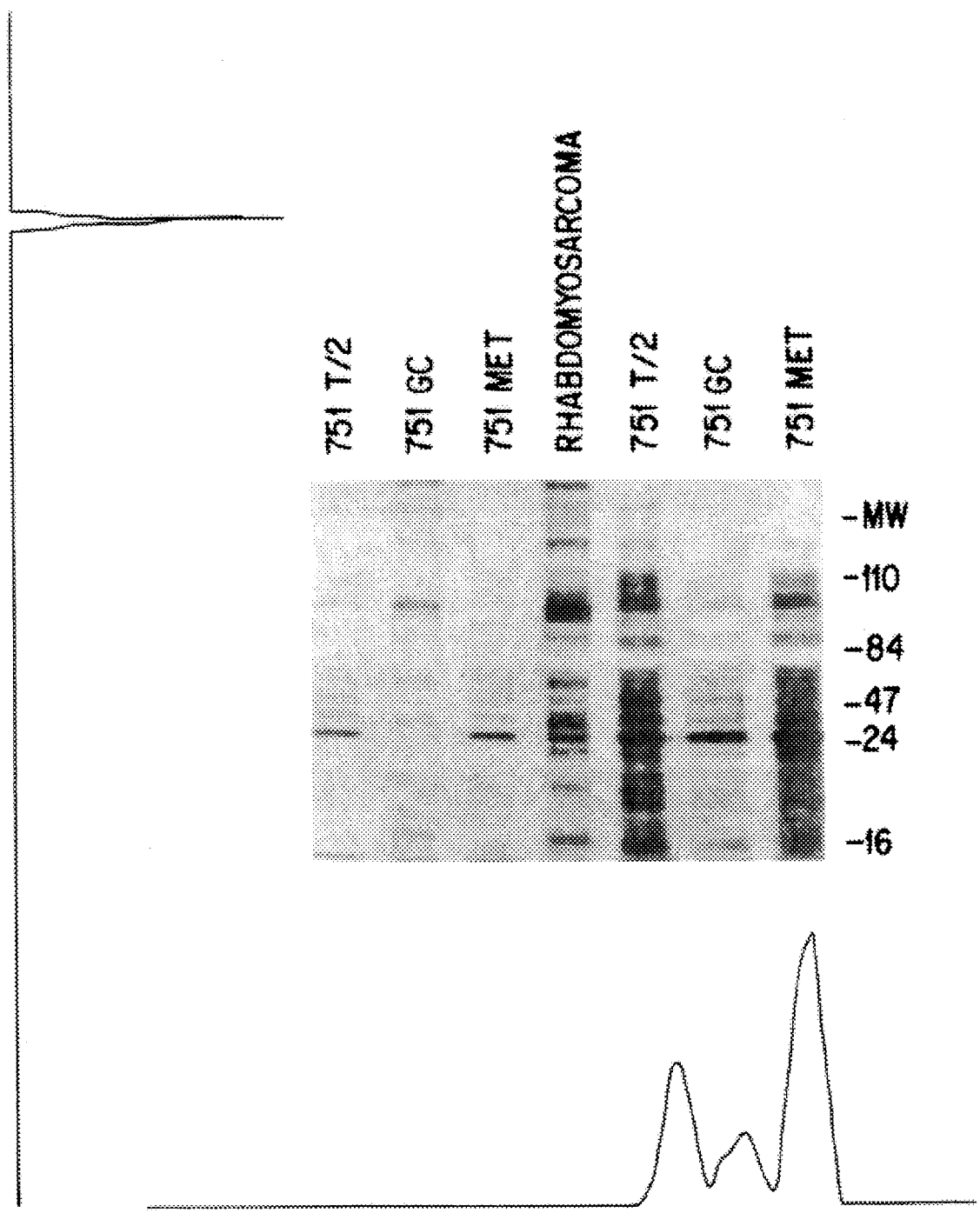

FIG. 2. Autoradiographs and Ambis scan of an SDS-PAGE gel of supernatants from 751 cells following [$^{35}$S]-methionine metabolic labelling. The supernatants were collected at 24 hours after $^{35}$S:-pulse -751-GC=original germ cell upon in vitro growth. 751-T2=nu/nu murine passaged cells isolated from the primary subcutaneous tumor. 751-Met nu/nu murine passaged cells isolated from a liver metastasis. The Ambis scan was directed against the 32 kDa protein and shows the quantitative difference in secretion, of the 32 kDa protein, from the murine tumor, metastasizing tumor and original germ cell line passaged only in tissue culture.

Figure 3A:
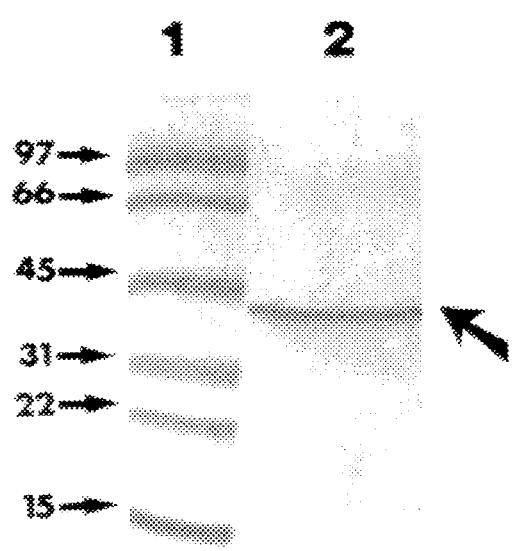
Figure 3B:
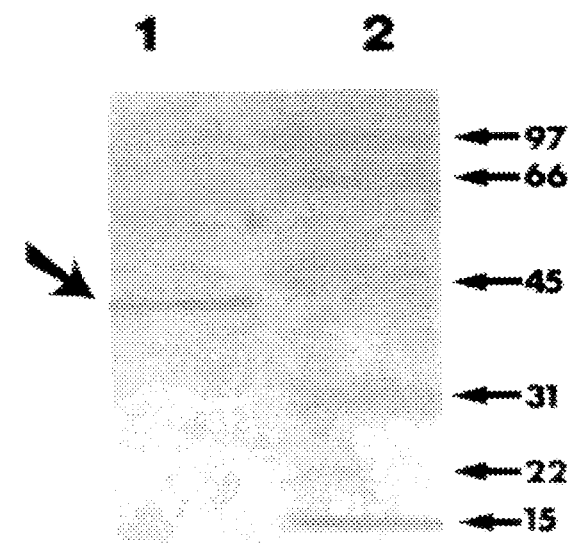

FIGS. 3A and 3B. Western blot analysis of the 37 kDa gel purified protein (SCPF) purified from 751 cells using SAM.1 antibody. FIG. 3A Coomassie blue stain of an SDS-PAGE gel showing the 37 kDa protein. FIG. 3B Western blot of the gel in panel FIG. 3A.

Figure 4:
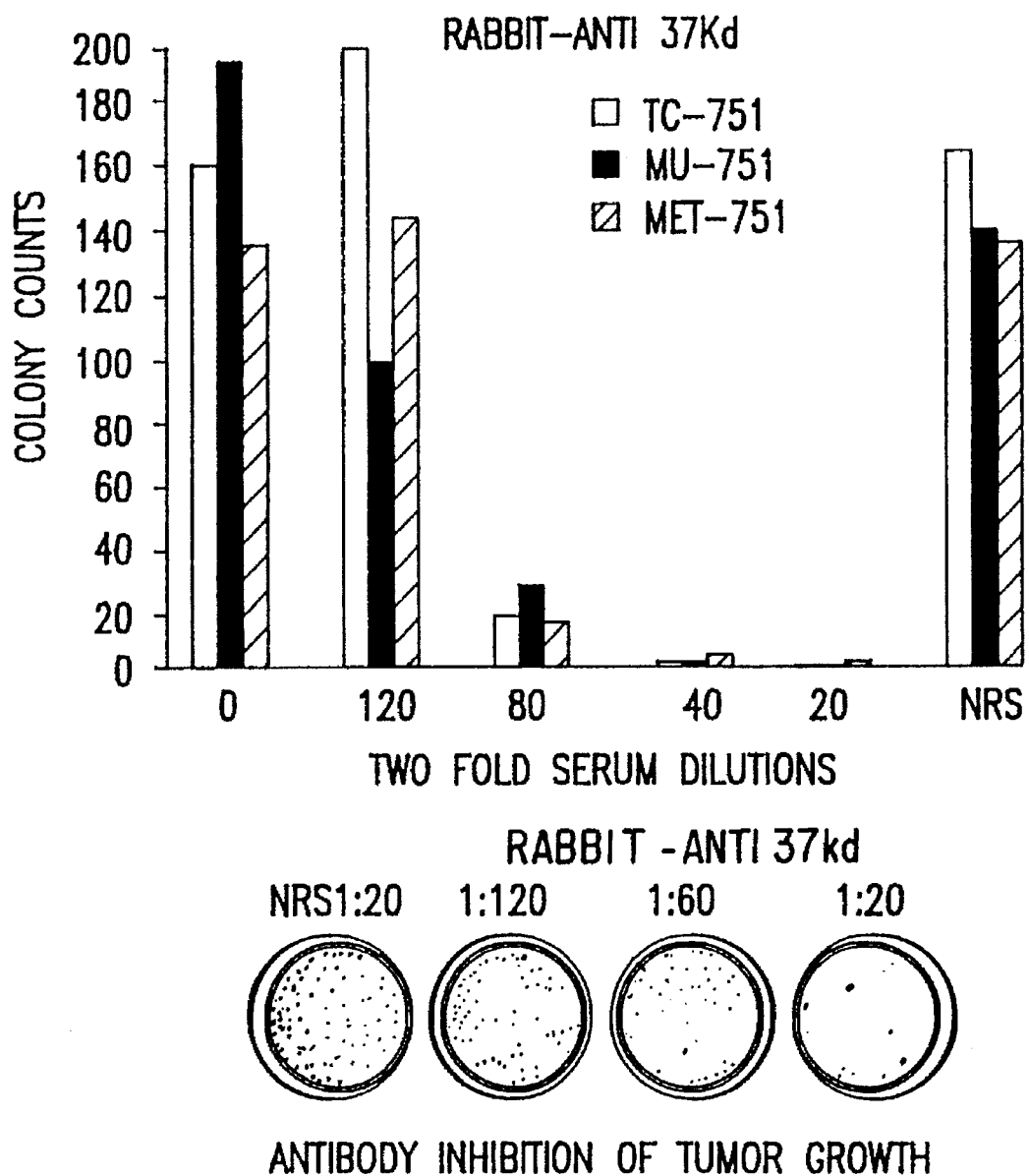

FIG. 4. Antibody inhibition of tumor growth. The SAM.1 antibody (anti-SCPF) was used to inhibit tumor cell colony formation in soft agar (methyl cellulose). The bar graph shows the inhibition of colonies (absolute numbers) as a function of antibody concentration. NRS is normal rabbit serum at a dilution of 1:20. The lower panel shows the actual colonies which are stained with methylene blue.

Figure 5:
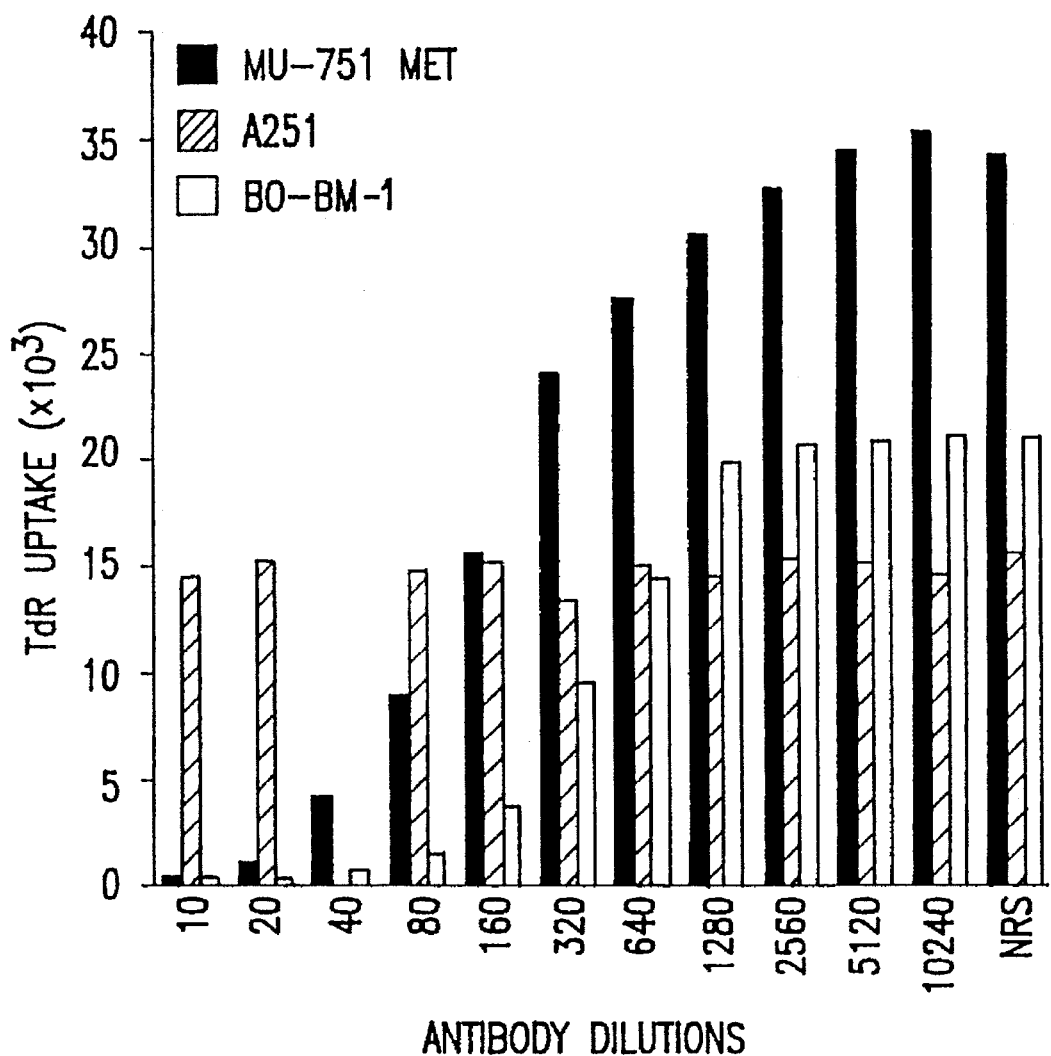

FIG. 5. Antibody inhibition of tumor growth. This figure shows the inhibition of tumor growth by the SAM.1 antibody as a function of tritiated thymidine incorporation to measure DNA replication. Cells were placed in 96-well microplates at 10,000 cells/well and antiserum at varying dilutions was added to each well. Each dilution was repeated in triplicate. 48 hours after culture the cells were labeled with $^3$H-thymidine (1 U/well) and recultured for 12 hours after which time the cells were harvested and the incorporation of the radioisotope measured using a scintillation counter. The data shows that the proliferation of the 751 cells and a very primitive bone marrow cell line (BO-BM.1) was inhibited by the antibody, however, A251 neuroblastoma cell line was not.

Figure 6:
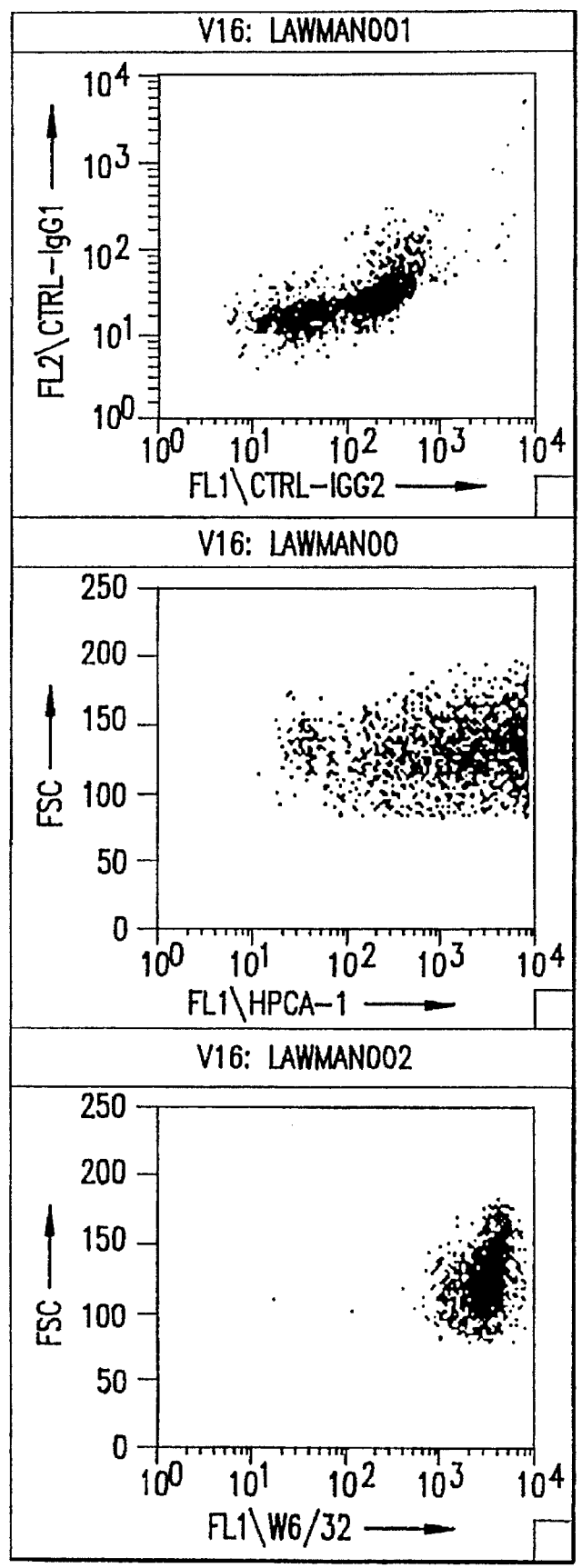

FIG. 6. Flow cytometric analysis of human bone marrow blast cells isolated from clonogenic activity: CD34 expression.

Figure 7:
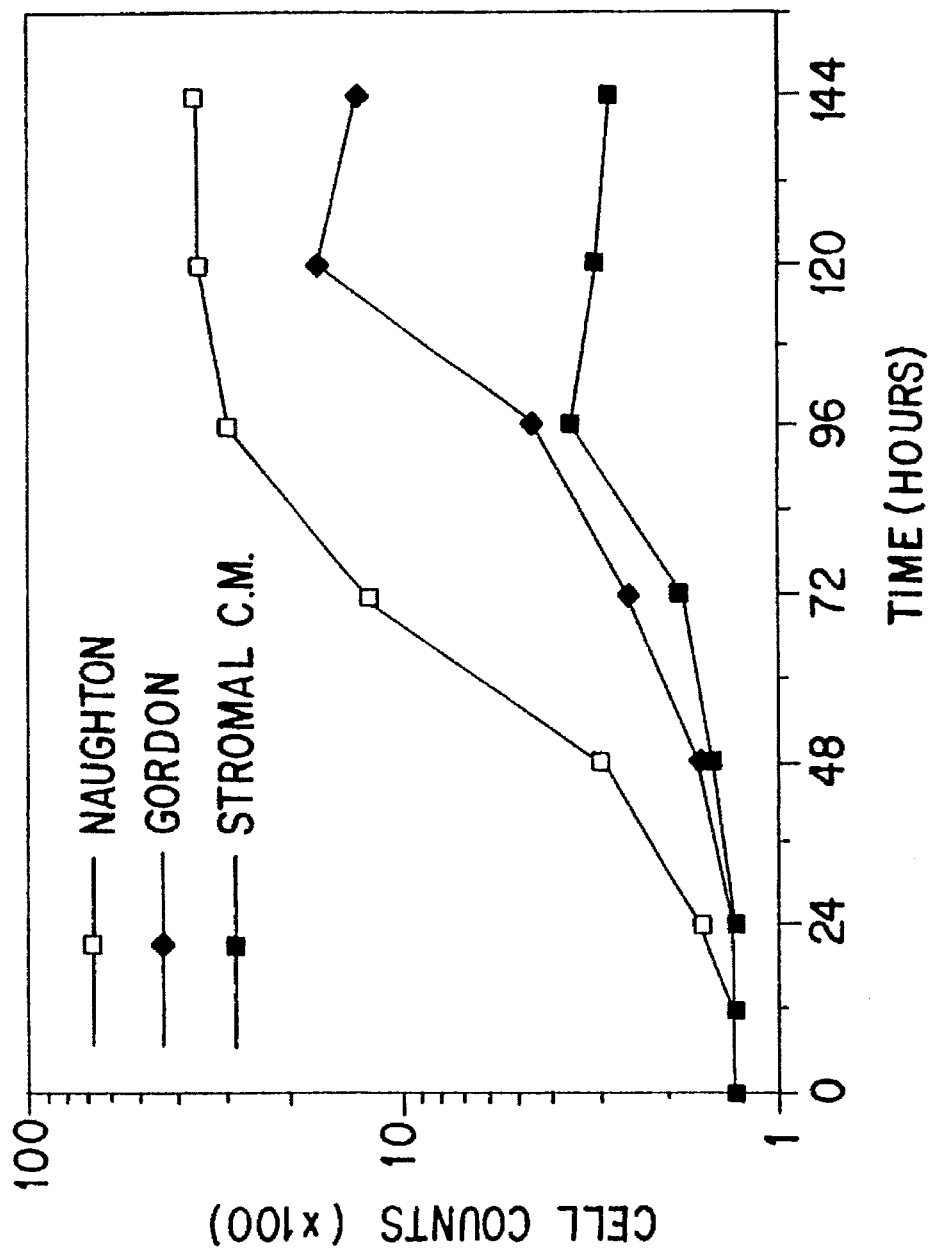

FIG. 7. Replication of the CD34$^+$ cells in long term in vitro culture: the CD34$^+$ cells were induced using SCPF purified from 751 cells prior to in vitro culture.

Figure 8:
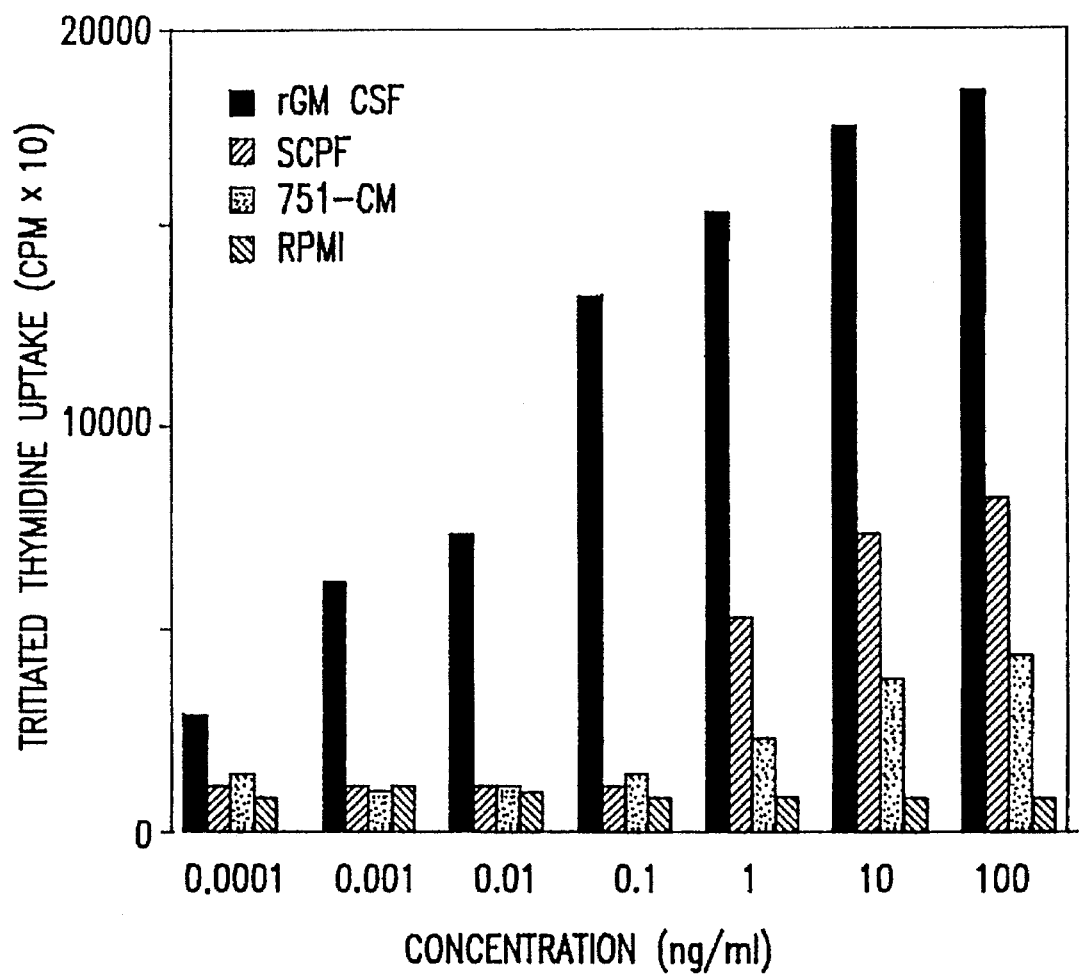

FIG. 8. Proliferation of normal human bone marrow in response to SCPF from 751 cells: Tritiated thymidine incorporation assay.

Figure 9A:
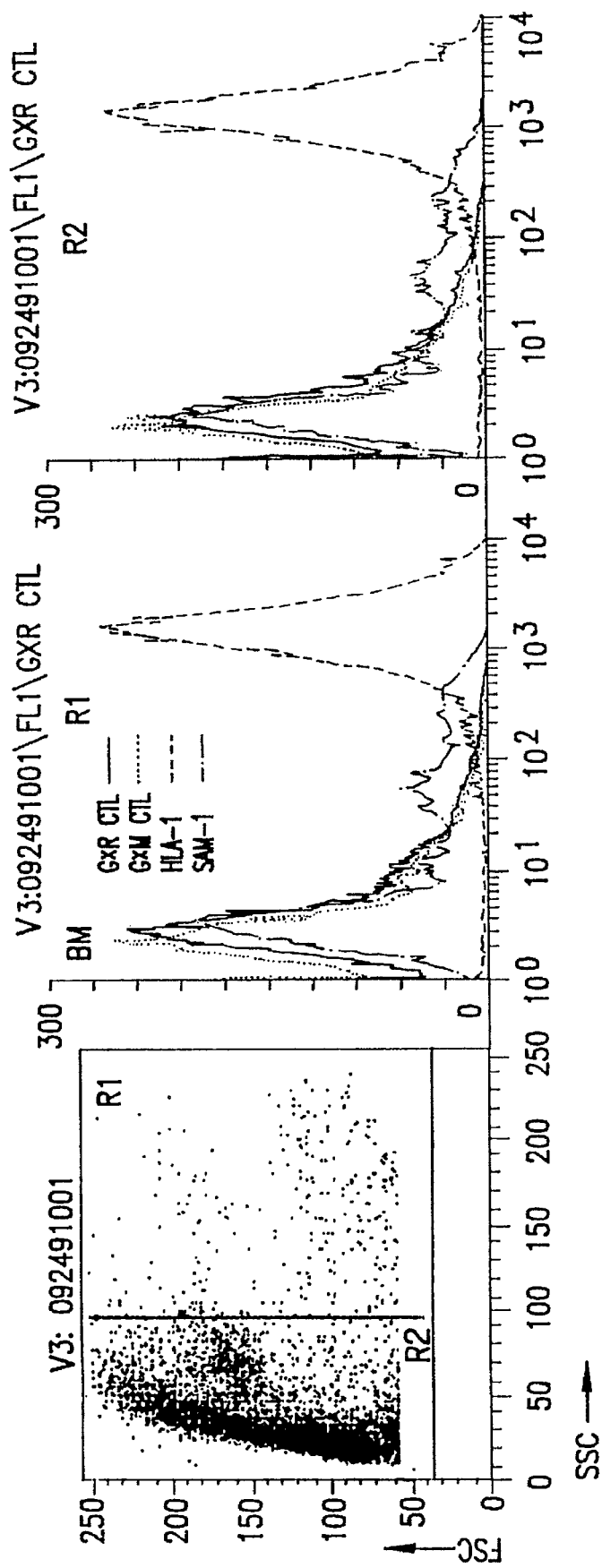
Figure 9B:
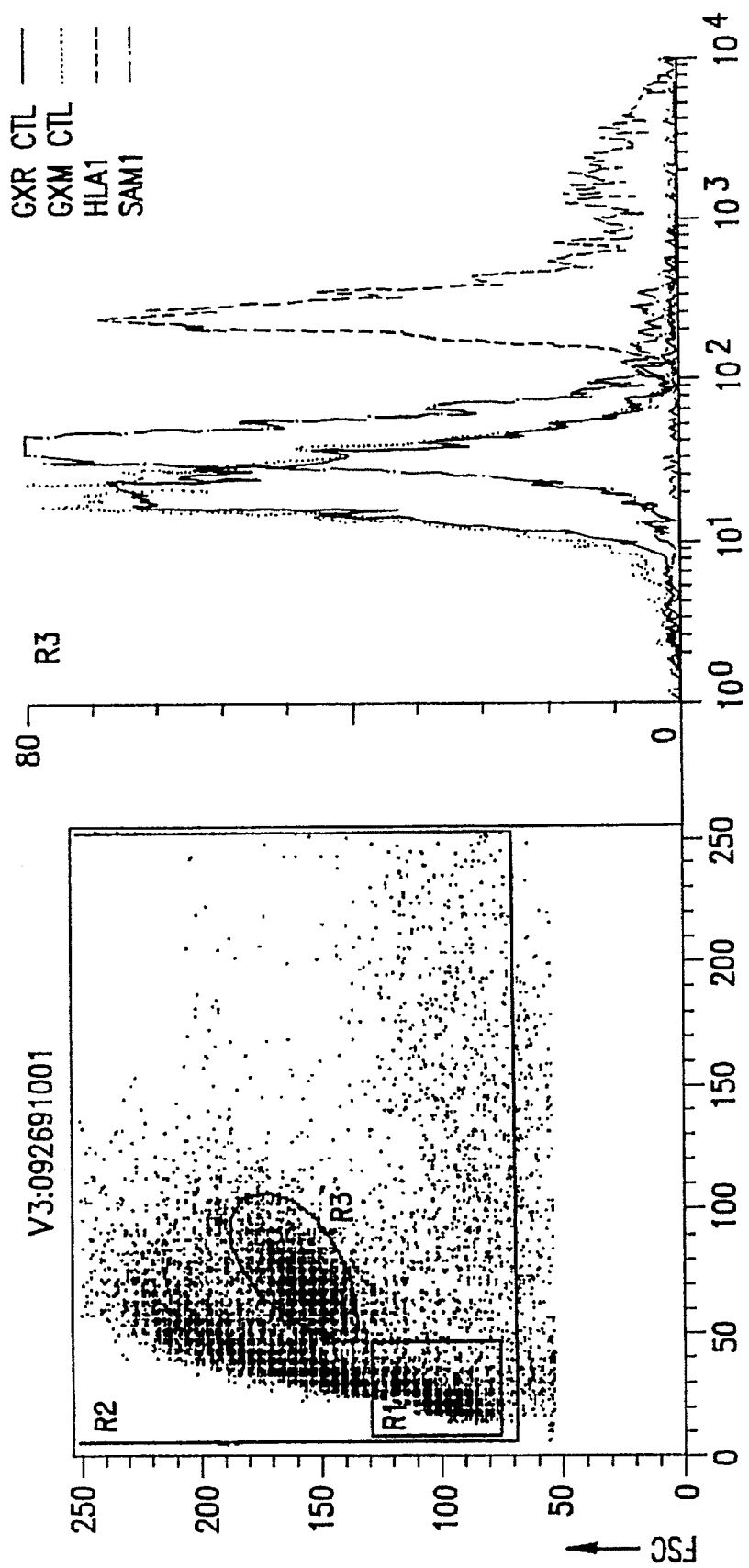

FIGS. 9A and 9B. Flow cytometric analysis of adherent depleted human bone marrow FIG. 9A and cord blood FIG. 9B stained with SAM.1 (anti-SCPF) antibody. The black line represents the FITC goat-anti-rabbit control, the blue line represents the goat anti-mouse FITC control. The HLA class I (green line) was used as a positive control.

Figure 10:
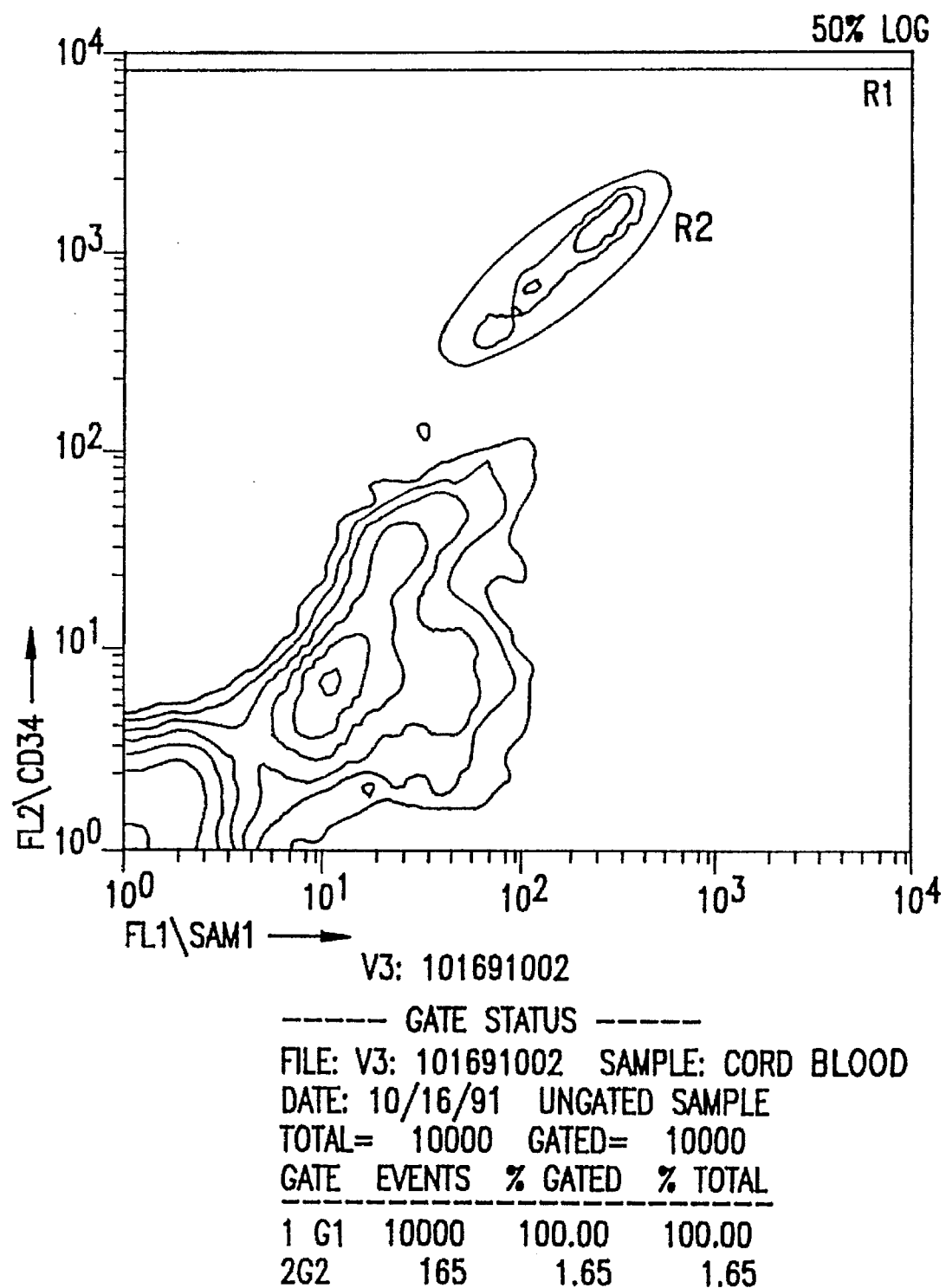

FIG. 10. Analysis of the dual staining (SAM.1 and CD34) population of human cord blood.

Figure 11:
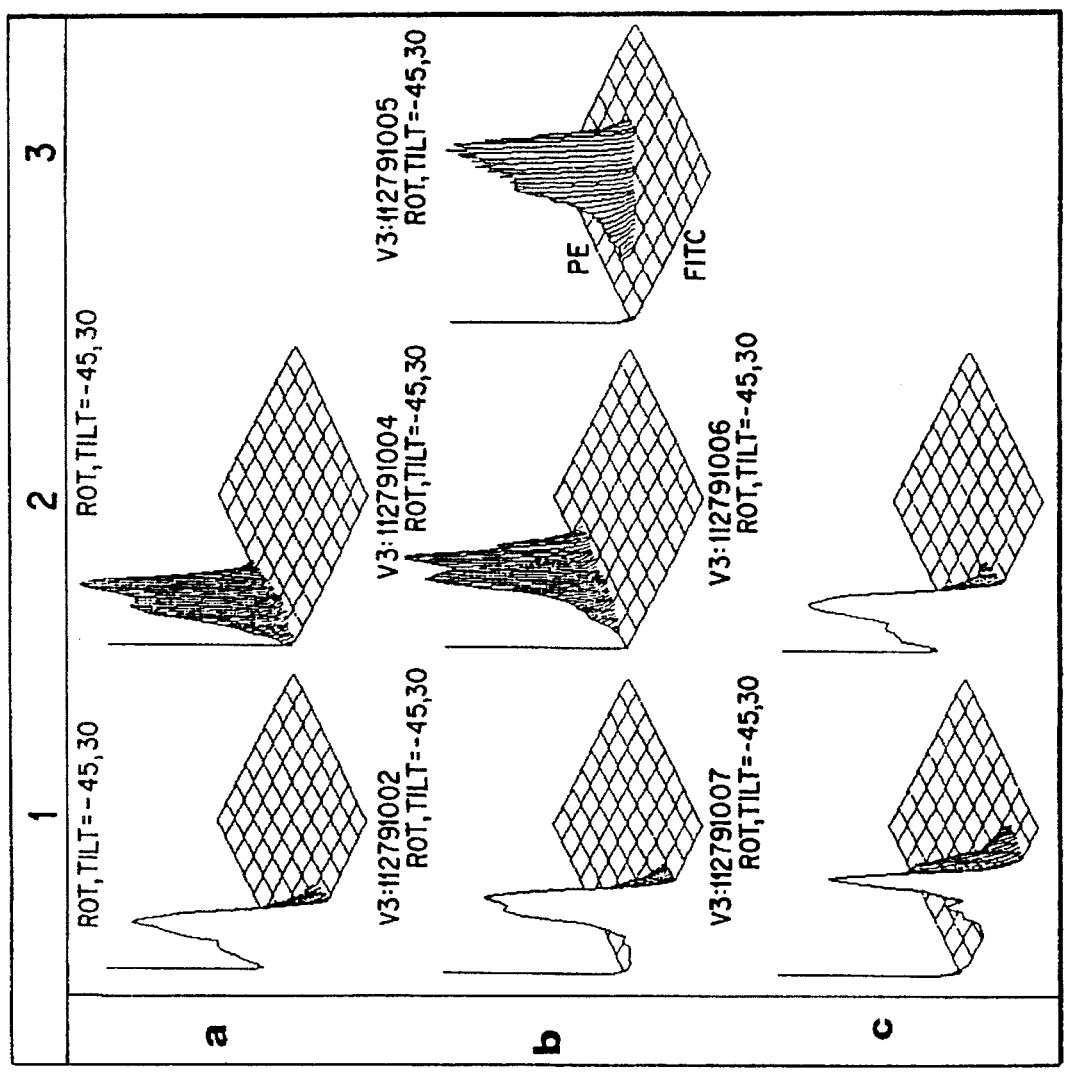

FIG. 11. Single and two color flow cytometric analysis of SAM.1 binding to CD34$^+$ cell isolated by immunomagnetic beads. (1a) goat-anti-rabbit FITC control, (1b) CD34$^+$ cells stained with SAM.1 antibody, (1c) CD34$^+$ cells stained with HLA class I mouse monoclonal antibody, (2a) goat-anti-mouse PE control, (2b) CD34$^+$ cells stained with anti-CD34 antibody, (2c) goat-anti-mouse FITC control, (3b) CD34$^+$ cells dual stained with SAM.1 (FITC) and anti-CD34 monoclonal antibody (PE).

Figure 12B:
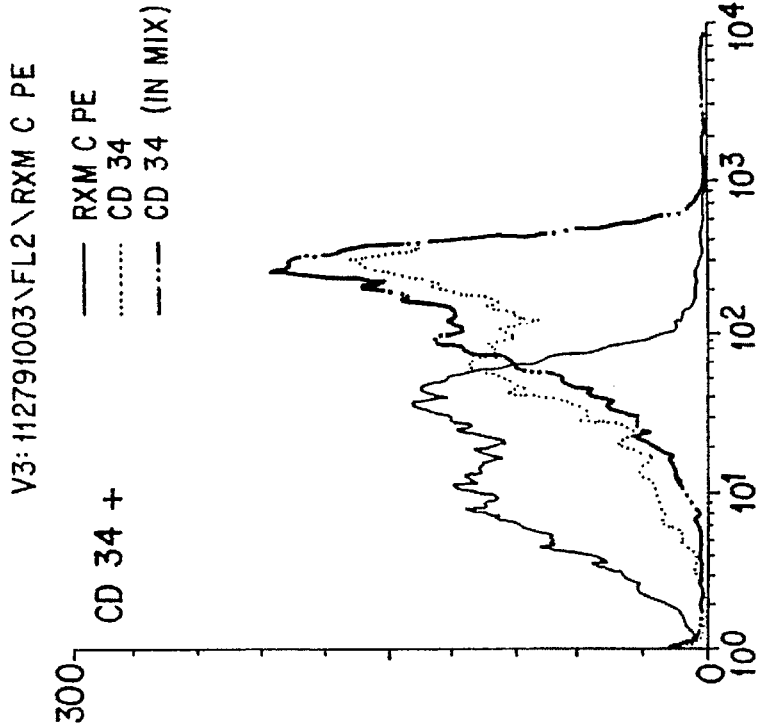
Figure 12A:
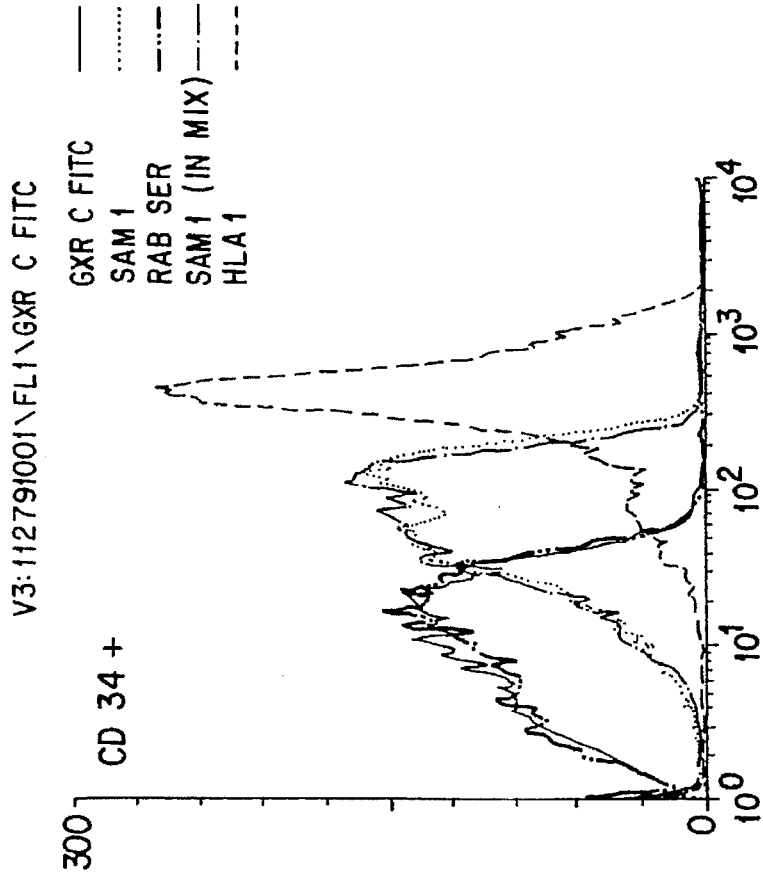

FIGS. 12A and 12B. Comparison, by flow cytometric analysis, of the binding efficiency of SAM.1 (FIG. 12A) and anti-CD34 alone (FIG. 12B) and in combination.

Figure 13:
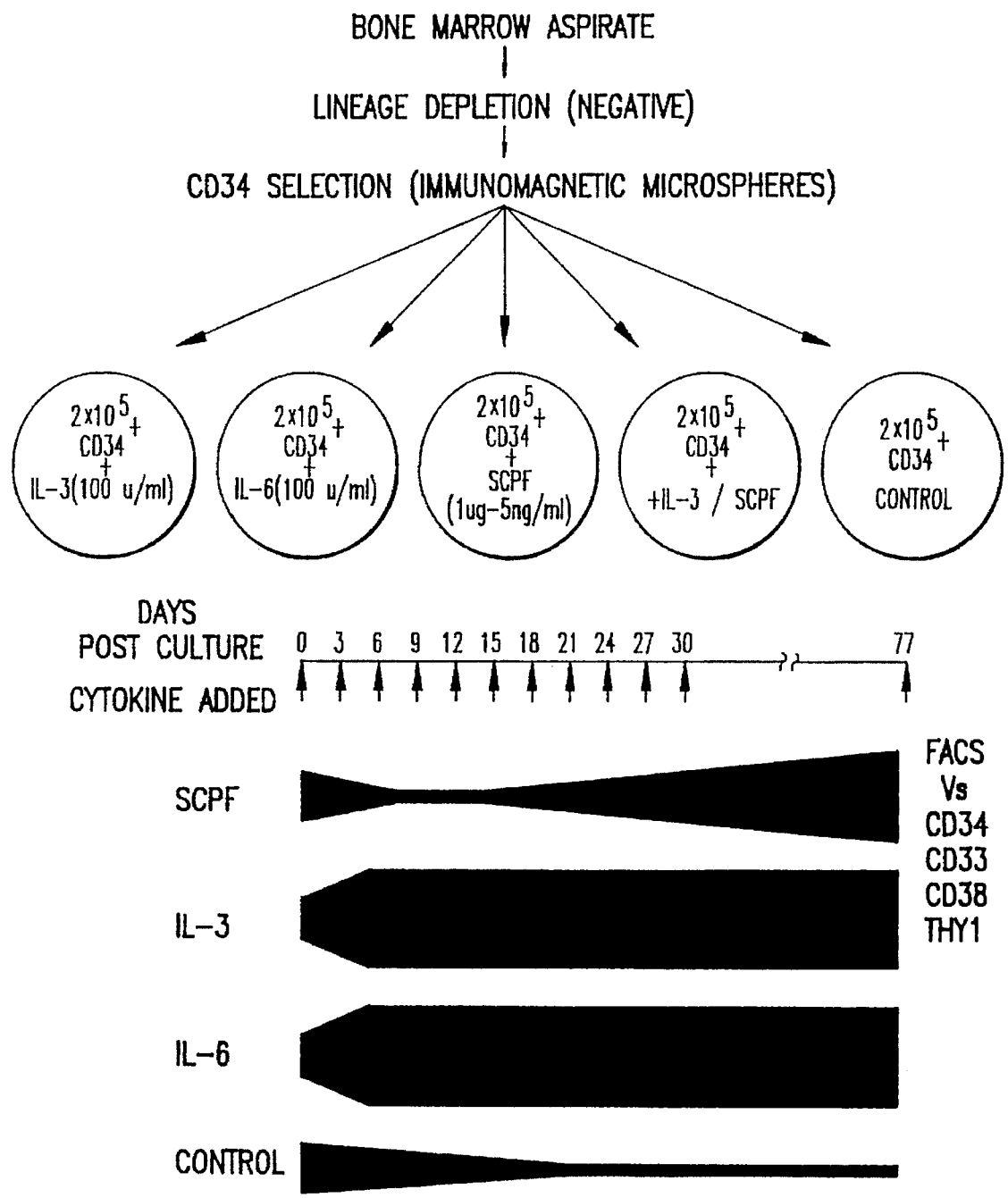

FIG. 13. Long term in vitro growth of CD34$^+$ cells using SCPF from 751 cells.

Figure 14:
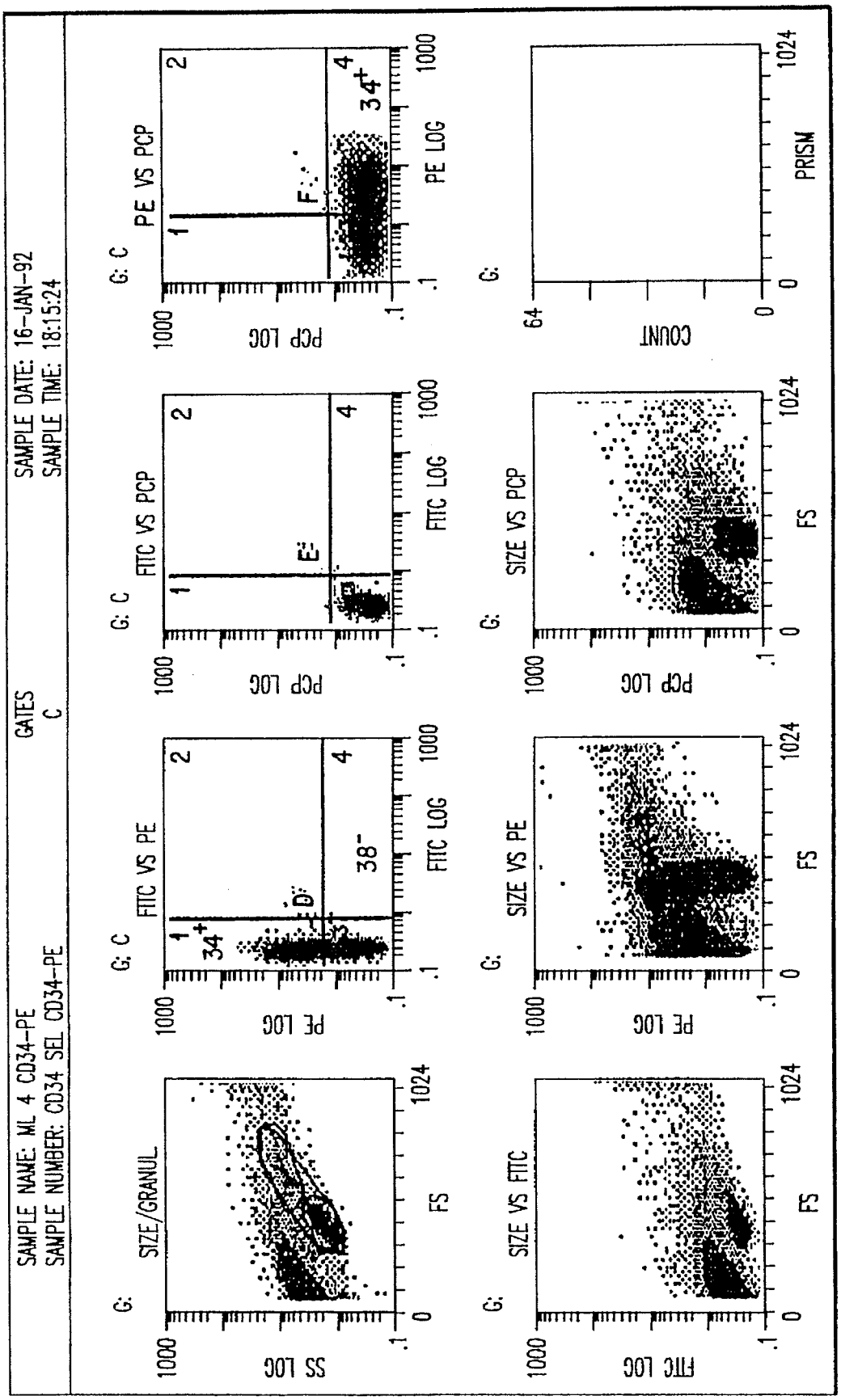

FIG. 14. Flow cytometric analysis (3 color) of the CD34$^+$ cells expanded in long-term culture using SCPF from 751 cells: Gate C.

Figure 15:
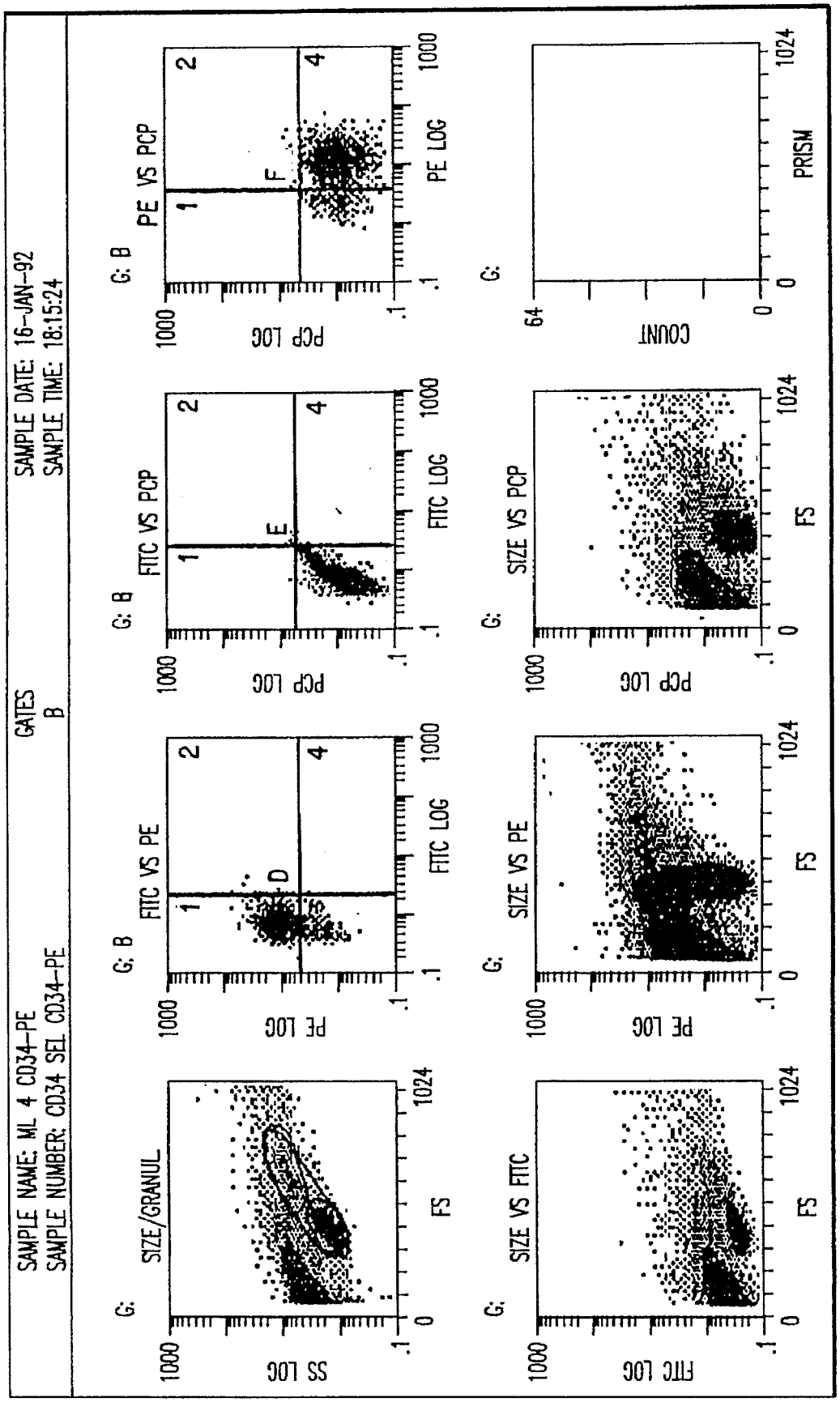

FIG. 15. Flow cytometric analysis (3 color) of the CD34$^+$ cells expanded in long-term culture using SCPF from 751 cells: Gate B.

Figure 16A:
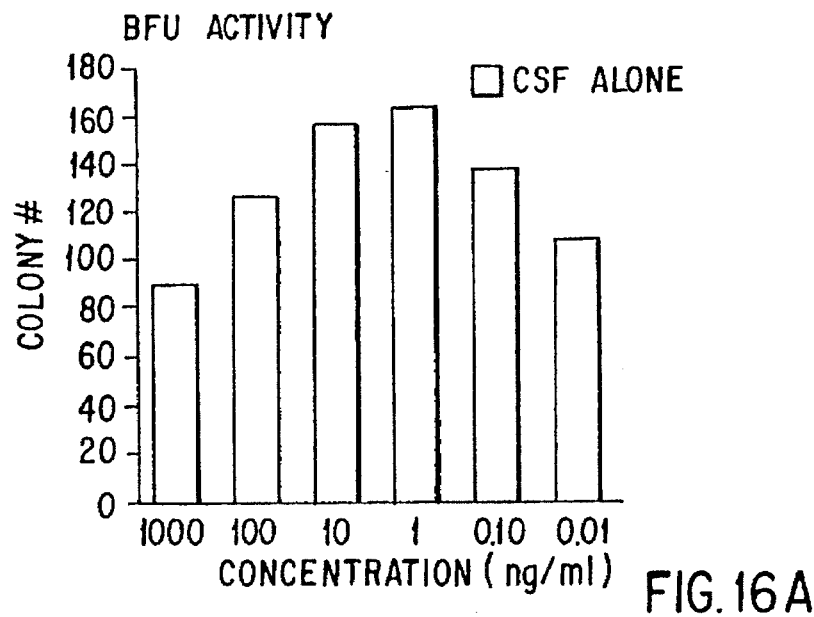
Figure 16B:
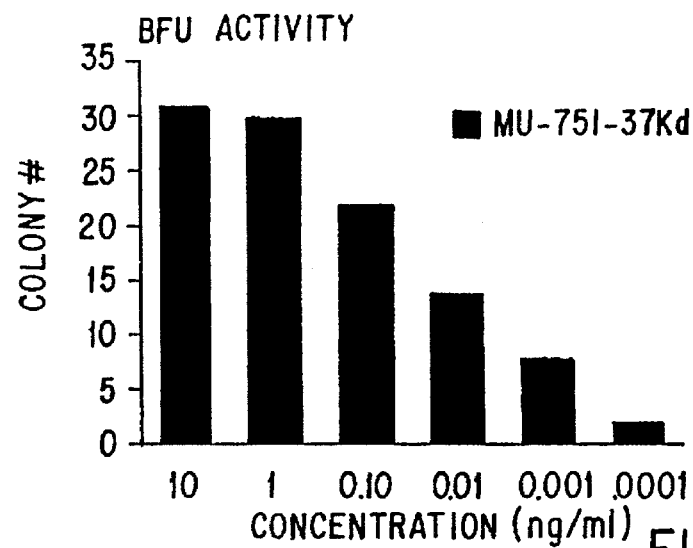
Figure 16C:
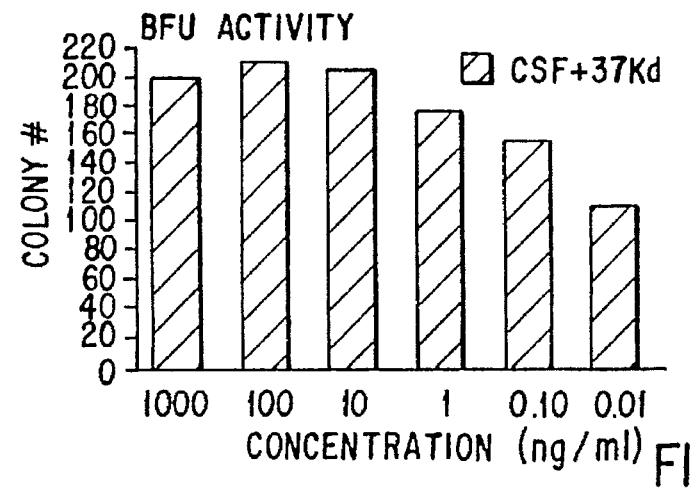

FIGS. 16A, 16B and 16C. Bone marrow clonogenic activity of SCPF from 751 cells. FIG. 16A BFU activity of a mixture of CSF's (100 u/ml GM-CSF, 100 u/ml IL-3, 1u/ml EPO) alone FIG. 16B BFU activity of SCPF at varying concentrations. FIG. 16C BFU activity of CSF mixed with 100 ng/ml of SCPF. The data indicates that SCPF is capable of inducing BFU activity alone FIG. 16B and also synergises with the CSF mixture FIG. 16C.

Figure 17A:
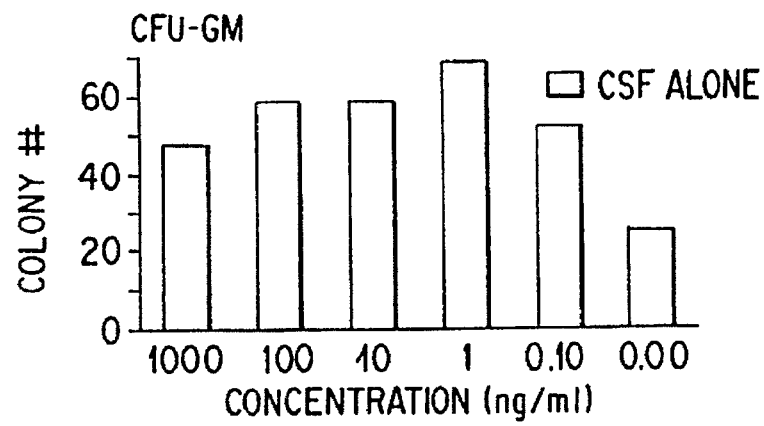
Figure 17B:
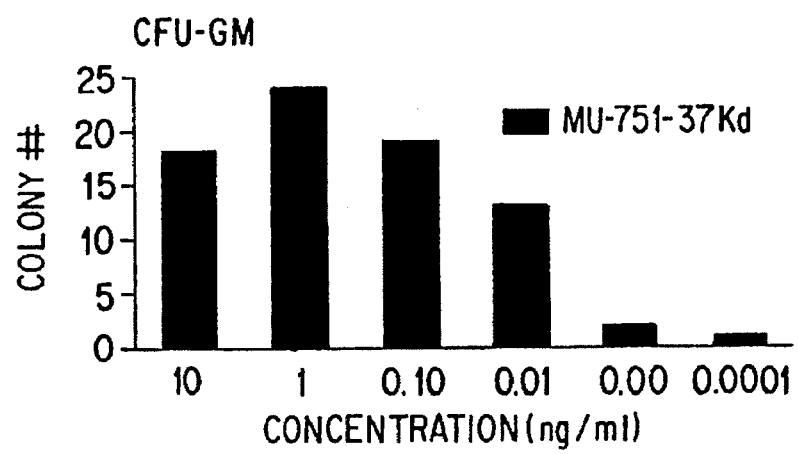
Figure 17C:
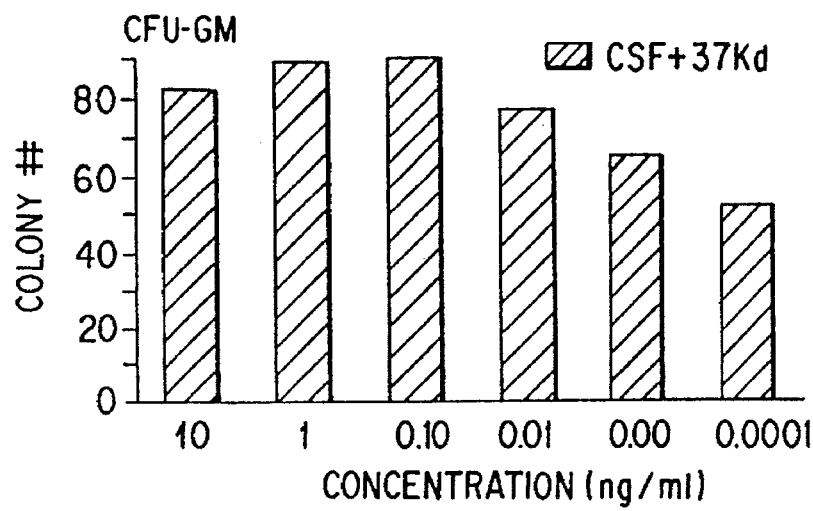

FIGS. 17A, 17B, and 17C. Bone marrow clonogenic activity of SCPF from 751 cells. FIG. 17A CFU-GM activity of a mixture of (100 u/ml GM-CSF, 100 u/ml IL-3, 1u/ml EPO) alone, FIG. 17B CFU-GM activity of SCPF at varying concentrations, FIG. 17C CFU-GM activity of CSF mixed with 100 ng/ml of SCPF. The data indicates that SCPF is capable of inducing CFU-GM activity alone FIG. 17B and also synergises with the CSF mixture FIG. 17C.

Figure 18A:
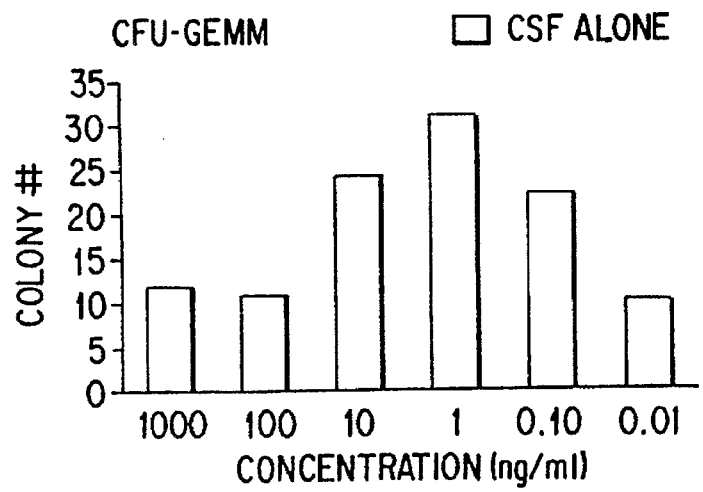
Figure 18B:
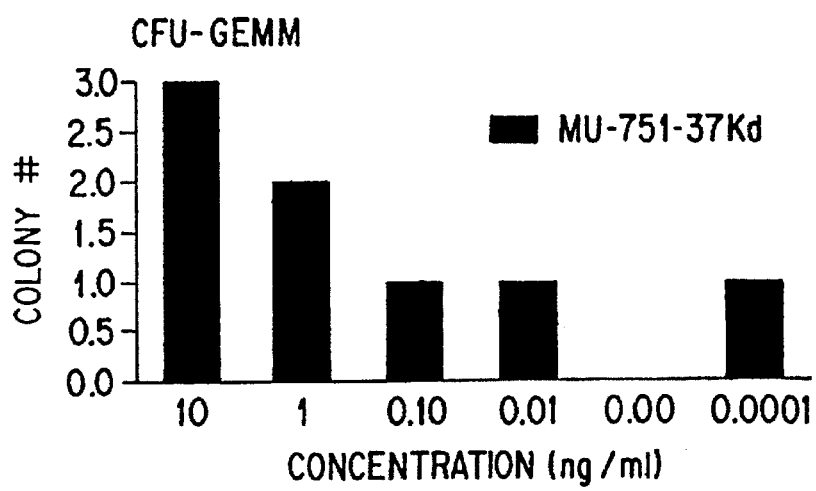
Figure 18C:
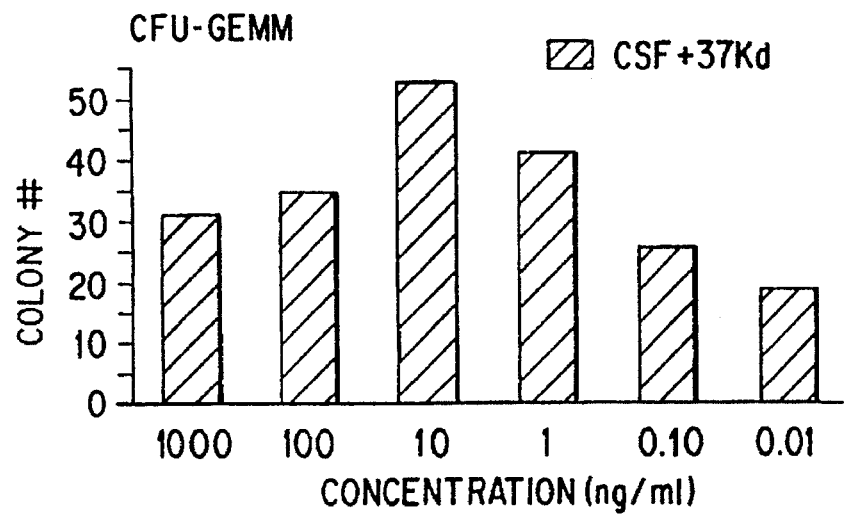

FIGS. 18A, 18B, and 18C. Bone marrow clonogenic activity of SCPF from 751 cells. FIG. 18A CFU-GEMM activity of a mixture of (100 u/ml GM-CSF, 100 u/ml IL-3, lu/ml EPO) alone. FIG. 18B CFU-GEMM activity of SCPF at varying concentrations. FIG. 18C CFU-GEMM activity of CSF mixed with 100 ng/ml of SCPF. The data indicates that SCPF is not capable of inducing CFU-GEMM activity alone FIG. 18B but will synergise with the CSF mixture FIG. 18C.

Figure 19:
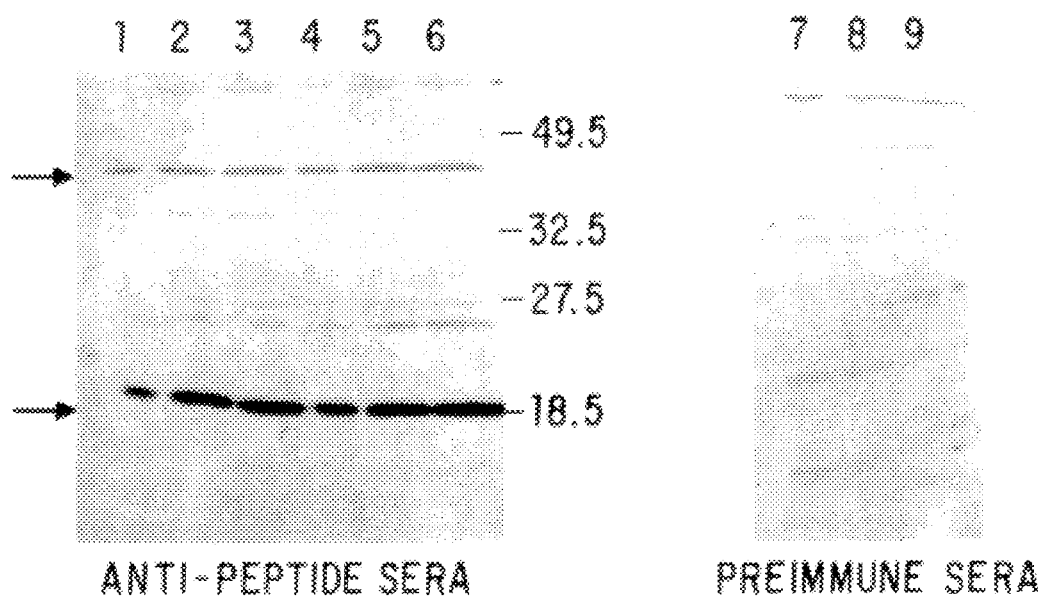

FIG. 19. Western blot analysis with anti-peptide antisera. Lanes 1, 2, and 3: 751 cell lysate (RPMI+10% FBS), 15 µl, 30 µl, and 40 µl, respectively; Lanes 4, 5, and 6: 751 cell lysate (RPMI+10% FBS)+50% serum-free supernatant from ML-1 cells; 15 µl, 30 µl, and 40 µl, respectively; Lanes 7, 8, and 9 show 30 µl of 751 NA cell lysate blotted with preimmune sera as a negative control.

Figure 20A:
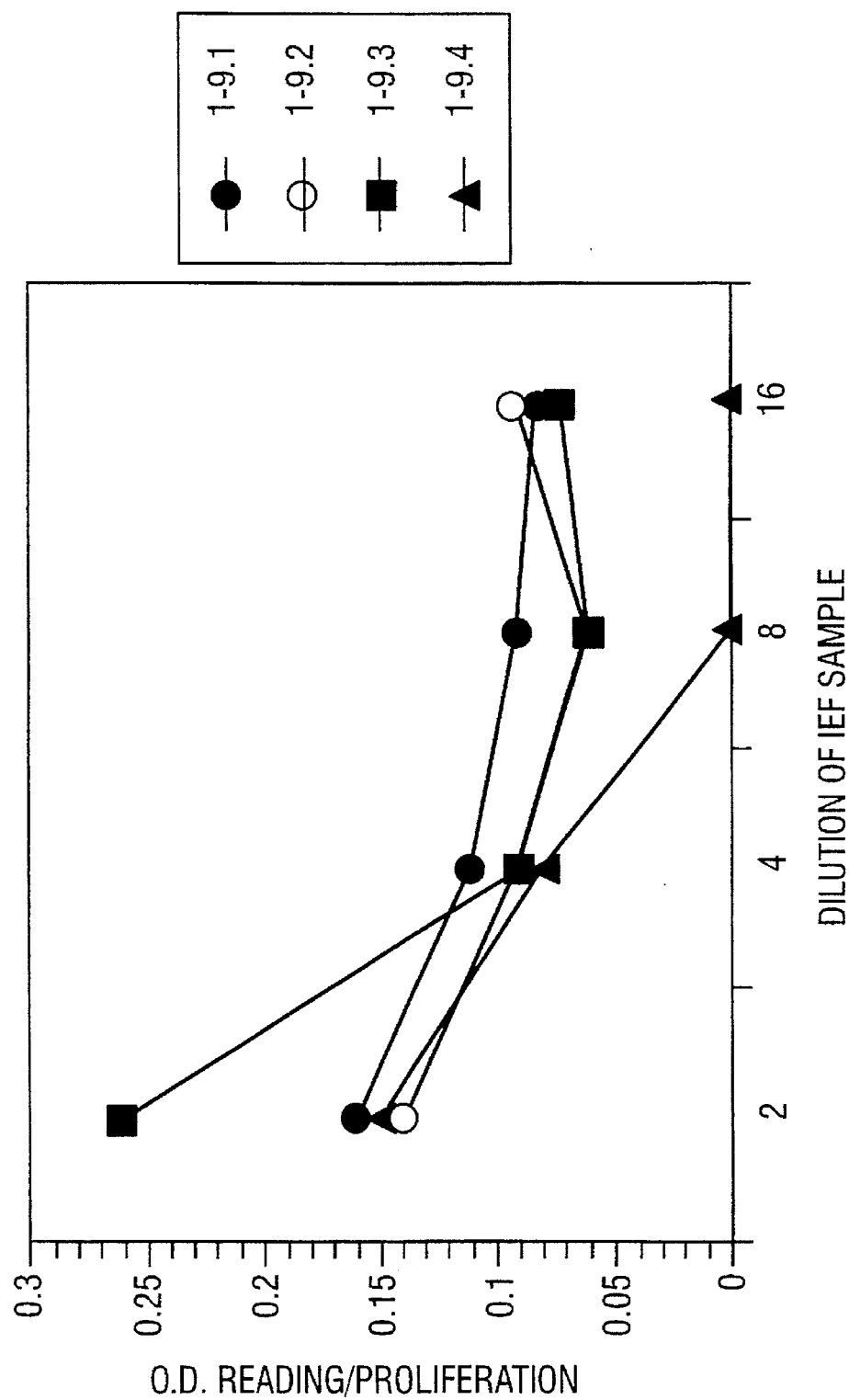
Figure 20B:
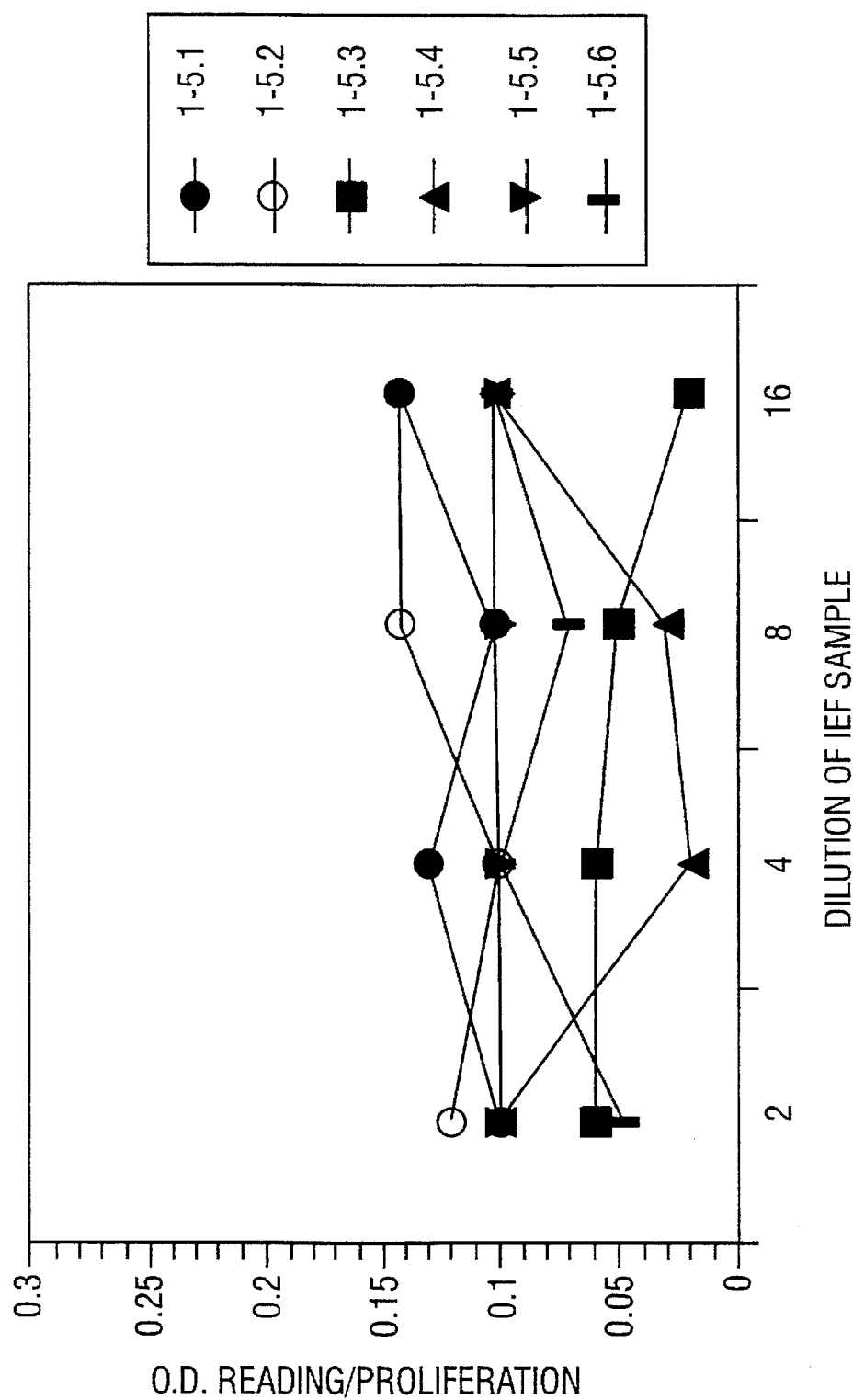

FIGS. 20A and 20B. Bioactivity of SCPF from ML-1 cells. FIG. 20A Cell proliferation by pH 9.0 region of an IEF gel. FIG. 20A cell proliferation by a pH 5.0 region of an IEF gel. The data indicates that bioactivity was present primarily in the material with pI 9.3 (27 kDa). No bioactivity was observed with any of the pH 5.0 region material.

Figure 21:
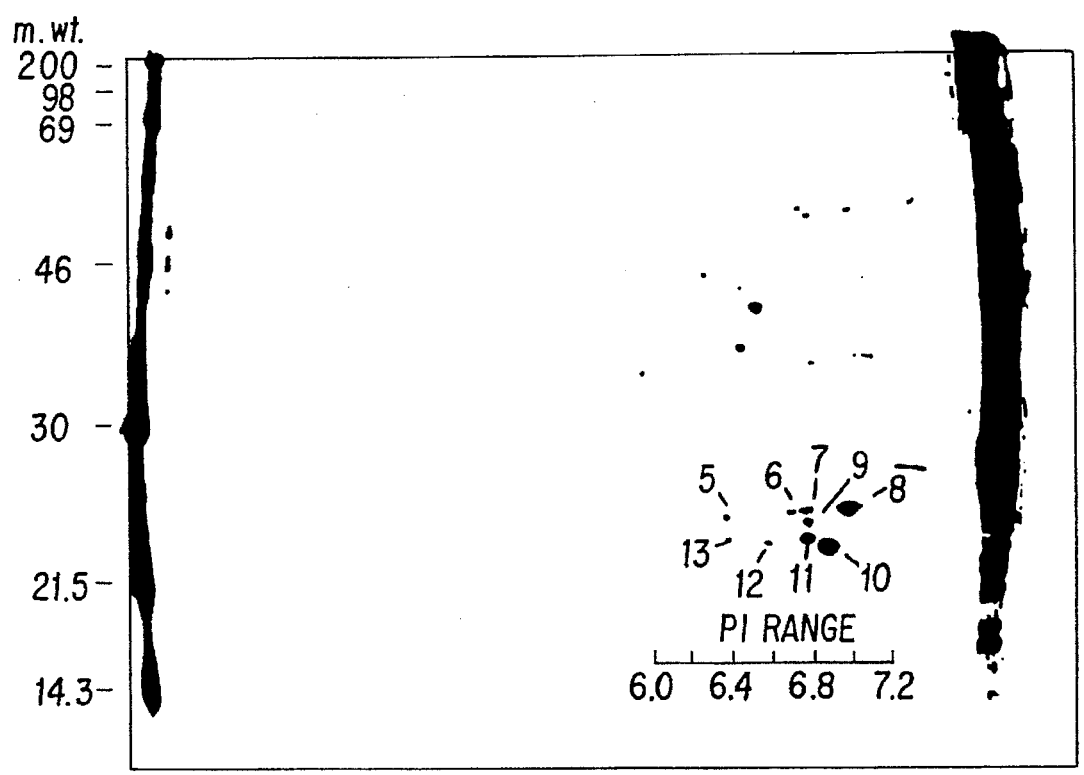

FIG. 21. 2-D Gel Electrophoresis of SCPF from ML-1 cells. The gel shows thirteen spots that resolved in the molecular weight range expected for SCPF from a 50 mM NaCl fraction from a Mono S column.

5. DETAILED DESCRIPTION OF THE INVENTION

The present invention relates to stem cell proliferation factor (SCPF), to methods for the production of SCPF by conventional or recombinant DNA technology, to methods of using SCPF, and to methods of identifying and isolating other members of the SCPF family from similarly derived cell lines.

SCPF, a novel autocrine growth factor, is expressed by murine cell line 751 in both membrane bound and secreted forms. The membrane form of SCPF is also expressed on the cell surface of a small fraction of CD34$^+$ human bone marrow cells. SCPF is expressed by CD34$^+$ human cell line ML-1 and has a molecular weight of 23 kDa and a pI of about 7.7, as isolated from cell lysates. Further, SCPF stimulates proliferation of CD34$^+$ bone marrow stem cells, indicating that it may be useful in conditions which require acceleration of hematopoietic cell growth, i.e., in the culture of stems cells for use in bone marrow transplantations, or treatment in vivo for regulating hematopoiesis. The removal of SCPF by an antibody in the 751 cell cultures leads to a reduction of tumor cell colony formation, suggesting that SCPF is involved in supporting tumor cell proliferation and thus, inhibition of SCPF activity may be useful in the treatment of certain tumors. This is further supported by in vivo experiments in which the co-injection of anti-SCPF antibody and 751 cells results in reduced tumorigenicity of the cell line. In addition, the membrane form of SCPF may also be useful as a cell surface marker for the identification and isolation of a small population of pluripotent bone marrow stem cells by use of an anti-SCPF antibody.

SCPF, or fragments and derivatives thereof, may have widespread potential applications in the regulation of hematopoiesis as well as in the treatment of certain germ cell cancers.

In another embodiment of the invention, germ cell tumor lines may be generated in culture. Such tumor cells may be a source of cytokines that possess growth potentiating activities on cells of the hematopoietic system in particular, and on germ/stem cells of a variety of tissue types in general.

The invention is discussed in more detail in the subsections below, solely for purposes of description and not by way of limitation. For clarity of discussion, the invention is described in terms of a particular SCPFs and cell lines. However, the principles may be analogously applied to other autocrine factors derived from other cell lines.

5.1. Cell Lines That Produce SCPF

Germ cell tumors of the central nervous system are believed to be products of primitive cells lodged in the neural crest during their migration to other tissue sites in embryogenesis. Such tumor cells may produce a variety of cytokines that act on tissues outside of the nervous system (Bhandar, 1988, Med. Hypoth, 27:291). Therefore, cell lines generated from germ cell tumors may be a source of early acting growth factors that influence proliferation of a variety of cell types, including cells of the hematopoietic system.

The murine cell line 751 was discovered in the course of establishing a cell line from a surgically removed germ cell tumor which was obtained from a patient diagnosed to have multiple subcutaneous masses along the ventriculoperitoneal shunt. The cultured 751 cells are non-adherent and display an extremely short doubling time of 7–8 hours in vitro. This rapid growth kinetic was also confirmed in vivo upon transfer of the cultured cells into BNX mice which developed visible subcutaneous tumors from an inoculum of $10^3$ cells in 7 days as opposed to 2–3 months for the majority of xenogeneic tumors in murine models.

Flow cytometry analysis using antibodies directed to specific cell determinants indicated that 751 cells represent a primitive brain neuro-ectodermal cell line which can further differentiate into neuronal or glial cell lineages upon appropriate stimulations. Therefore, it is a primitive pluripotent cell line possessing both growth and differentiation potentials. In addition, mRNA's for the oncogenes c-myc and c-fms have been detected using molecular probes specific for a panel of oncogene sequences. As c-fms has been shown to be a receptor for macrophage-colony stimulating factor, 751 cells may be related in some manner to progenitor cells of the bone marrow.

The ML-1 cell line was established by treating a heterogeneous population of CD34$^+$ human bone marrow cells with a partially purified SCPF fraction obtained from the 751 cells, as described infra. The cells were subcultured in the presence of the 751 SCPF preparation as described infra, and the ML-1 cell line, which is capable of continuous growth in the absence of exogeneous SCPF, was isolated. This cell line is shown to be CD34$^+$, CD38$^-$, HLADR$^+$, but CD3$^-$, CDR$^-$ and CD8$^-$.

5.2. Stem Cell Proliferation Factor

The stem cell proliferation factor produced by the 751 cell line as described in the examples herein, exists in two forms, a secreted form having a molecular weight of about 32 kDa, and a membrane bound form of 37 kDa in molecular weight. Multiple isoforms of the SCPF are identified having P.I.'s ranging from about 7.0 to 8.0.

The 32 kDa SCPF was used to generate a polyclonal antiserum in rabbits. A specific polyclonal antibody designated SAM.1 was used to facilitate further biochemical characterization of the major secreted protein by 751 cells. The antibody was first shown to be specific for the SCPF protein, as it reacted with a protein species of 37 kDa in 751 whole cell lysates in Western immunoblotting experiments. This finding demonstrates that the protein of interest can exist in a secreted form of 32 kDa and a membrane form of 37 kDa molecular weight which may include a transmembrane component for anchoring. Thus, the same protein may function as both a soluble molecule and a cell surface protein between interacting cells.

In order to delineate the biologic activities of this protein (referred to hereafter as stem cell proliferation factor, SCPF), colony inhibition assays were performed in which 751 cell colony formation was assessed in the presence of various concentrations of the rabbit antiserum. The results clearly demonstrate that the antibody inhibited the tumor cell colony formation, indicating that the secreted protein is an autocrine growth factor which promotes the growth of 751 cells. Furthermore, the proliferation inhibitory effect of the antibody is specific for germ or stem cell lines in that growth of a neuroblastoma cell line is not inhibited.

SCPF was purified from the murine 751 cell line and tested for its ability to stimulate the proliferation of human bone marrow cells. SCPF induced the growth of blast cells in clonogenic assays, which were subsequently shown to express the CD34 marker and HLA Class I antigen by flow cytometric analysis. When the same cells were grown in long term Gordon cultures in the absence of SCPF and tested for replating efficiency in the presence of recombinant GM-CSF, the cells responded to give rise of colonies of granulocytes, monocytes and mixed phenotype. Therefore, SCPF is capable of inducing replication of a population of $CD34^+$ bone marrow cells which retain ability to differentiate in response to subsequent stimulation with colony stimulating factors.

When anti-SCPF antibody was reacted with human bone marrow cells, a small but detectable fraction of cells were shown to be positively stained. The same cells also express the CD34 protein which has been reported to be a marker expressed by hematopoietic stem cells. However, the finding that the SCPF-producing 751 germ cell tumor is negative for CD34 expression and that anti-SCPF and anti-CD34 antibodies do not competitively inhibit each other in binding to purified $CD34^+$ cells, demonstrate that the SAM.1 antibody is not directed to the CD34 marker but to a membrane form of SCPF. SAM.1 antibody does not cross-react with any proteins of different non-human animal species, as it failed to react with cells obtained from murine, bovine and ovine bone marrow.

In order to further characterize the biological properties of SCPF, long-term cultures of $CD34^+$ cells were initiated in the presence of exogenous SCPF purified from cell line 751. Unlike the cultures that expanded rapidly in response to recombinant IL-3 or IL-6, cultures receiving SCPF underwent an initial phase of cell death leading to a residual population of $CD34^+$ cells which could then proliferate in response to SCPF. The SCPF-treated cells appear more uniform in morphology, in contradistinction to the cultures grown in IL-3 or IL-6. However, the SCPF-treated cultures generated two cell populations based on cell surface marker expression. While both populations expressed CD34, one population was negative for CD38 and HLA-DR expression and the other expressed low levels of both markers. Thus, taken collectively, SCPF is an autocrine growth factor that induces the proliferation of $CD34^+$ bone marrow cells without causing differentiation while the cells retain their capacity to respond to other differentiation signals. The factor does not induce malignant transformation of cultured cells because the removal of SCPF led to a rapid decline in $CD34^+$ cell viability.

Additionally, SCPF is capable of augmenting the stimulatory effects on bone marrow cells when used in combination with other colony stimulating factors. However, SCPF biological activity is not similar to any of the known hematopoietic growth factors including GM-CSF, G-CSF, M-CSF and IL-3. In addition, antibodies specific for human GM-CSF, G-CSF, M-CSF and IL-3 do not neutralize the biologic activities of SCPF. Furthermore, anti-SCPF antibody does not inhibit the function of a recently identified stem cell factor (SCF) which has been shown to be the ligand for a receptor encoded by the c-kit oncogene (Yokota et al., 1984, Proc. Natl. Acad. Sci. U.S.A. 81:1070; Williams et al., 1990, Cell 63:167; Zsebo et al., 1990, Cell 63:195).

SCPF produced by the murine 751 cells was utilized to enhance the isolation of the ML-1 cell line as described in the examples, infra. The ML-1 cell line is both a target cell for SCPF activity and a source of human SCPF. The SCPF obtained from ML-1 cell lysates exhibits a molecular weight of 23 kDa and a pI of about 7.7 as determined by two dimensional gel electrophoresis in the presence or urea described infra. The SCPF produced by ML-1 reacts with SAM.1 antibody (which was generated against SCPF from 751 cells) and demonstrates bioactivity when assayed on human target cells as described infra.

5.3. Isolation of the SCPF Coding Sequence

Messenger RNA (mRNA) for the preparation of cDNA may be obtained from cell sources that produce SCPF, whereas genomic sequences for SCPF may be obtained from any cell source. For example, ML-1, 751-NA, 751-LIV or 751-LN cells may be utilized either as the source of the coding sequences for SCPF and/or to prepare cDNA or genomic libraries. Genetically-engineered microorganisms or cell lines containing the SCPF coding sequence may be used as a convenient source of DNA for this purpose.

Either cDNA or genomic libraries may be prepared from the DNA fragments generated using techniques well known in the art. The fragments which encode SCPF may be identified by screening such libraries with a nucleotide probe homologous to a portion of the SCPF sequence which is based on amino acid sequence information obtained from the purified protein. Alternatively, an antibody probe may be used to screen a library generated by expression cloning methods such as λgt11 (Young and Davis, Proc. Natl. Acad. Sci. U.S.A. 80:1194–1198). Although portions of the coding sequence may be utilized for cloning and expression, full length clones, i.e., those containing the entire coding region for SCPF, may be preferable for expression. To these ends, techniques well known to those skilled in the art for the isolation of DNA, generation of appropriate restriction fragments, construction of clones and libraries, and screening recombinants may be used. Oligonucleotide sequences can be used to increase the copy number of a unique gene sequence by the polymerase chain reaction. This approach would provide for more specific probes than that obtained using degenerate oligonucleotides. See, for example, the techniques described in Maniatis et al., 1989, Molecular Cloning, A Laboratory Manual, Cold Spring Harbor Laboratory, N.Y.

Regardless of the method chosen to identify and clone the SCPF coding sequence, expression cloning methods may be utilized to substantially reduce the screening effort. Recently, a one step procedure for cloning and expressing antibody genes has been reported (McCafferty et al., 1990, Nature 348:552–554; Winter and Milstein, 1991, Nature 349: 293–299). Based on this technology, the SCPF gene may likewise be cloned directly into a vector at a site adjacent to the coat protein gene of a bacteriophage such as λ or fd. The phage carrying the SCPF gene expresses the fusion protein on its surface so that columns containing an SCPF-specific antibody can be used to select and isolate phage particles with binding activity. A commercially available expression cloning system utilizing Lambda-Zapbluescript (Stratagene, La Jolla, Calif.) may also be used for the cloning and antibody screening of SCPF cDNA libraries. Transient gene expression systems may be utilized to identify the correct SCPF gene. For example, the COS cell system (e.g., Gerard & Gluzman, 1986, Mol. Cell. Biol. 6(12) 4570–4577) may be used.

Due to the degeneracy of the nucleotide coding sequences, other DNA sequences which encode amino acid sequences of any SCPF gene product may be used in the practice of the present invention for the cloning and expression of SCPF. For example, nucleotide sequences which encode the SCPF amino acid sequence, or which selectively hybridize to the SCPF gene or its cDNA, may be utilized for cloning and expression of SCPF. Such sequence alterations may include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

In addition, other DNA sequences containing structural modifications which do not substantially alter the biologic activities of the encoded SCPF protein may also be used in the practice of the invention. Such modifications include but are limited to additions, deletions or substitutions of amino acid residues in SCPF to create additional processing sites and/or elimination of glycosylation sites. For example, the removal of N-linked glycosylation sites in certain proteins results in reduced glycosylation of the expressed products which are particularly useful in yeast expression systems.

5.4. Expression of SCPF by Recombinant DNA Technology

In order to express a biologically active SCPF, the nucleotide sequence encoding SCPF, or a functionally equivalent nucleotide sequence, is inserted into an appropriate expression vector, i.e., a vector which contains the necessary elements for the transcription and translation of the inserted coding sequence. Modified versions of the SCPF coding sequence could be engineered to enhance stability, production, purification or yield of the expressed product. For example, the expression of a fusion protein or a clearable fusion protein comprising SCPF and a heterologous protein may be engineered. Such a fusion protein may be readily isolated by affinity chromatography; e.g. by immobilization on a column specific for the heterologous protein. Where a cleavage site is engineered between the SCPF moiety and the heterologous protein, the SCPF protein can be released from the chromatographic column by treatment with an appropriate enzyme or agent that disrupts the cleavage site (e.g., see Booth et al., 1988, Immunol. Lett. 19:65–70; and Gardella et al., 1990, J. Biol. Chem. 265:15854–15859).

Methods which are well known to those skilled in the art can be used to construct expression vectors containing the SCPF coding sequence and appropriate transcriptional/translational control signals. These methods include in vitro recombinant DNA techniques, synthetic techniques, and in vivo recombination/genetic techniques. See, for example, the techniques described in Maniatis et al., 1989 Molecular Cloning A Laboratory Manual, Cold Spring Harbor Laboratory, N.Y.

A variety of host-expression vector systems may be utilized to express the SCPF coding sequence. These include but are not limited to microorganisms such as bacteria transformed with recombinant bacteriophage DNA, plasmid DNA or cosmid DNA expression vectors containing the SCPF coding sequence; yeast transformed with recombinant yeast expression vectors containing the SCPF coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the SCPF coding sequence; insect cell systems infected with recombinant virus expression vectors (e.g., baculovirus) containing the SCPF coding sequence; or animal cell systems infected with recombinant virus expression vectors (e.g., retroviruses, adenovirus, vaccinia virus) containing the SCPF coding sequence, or transformed animal cell systems engineered for stable expression. Since SCPF has not been confirmed to contain carbohydrates, both bacterial expression systems as well as those that provide for translational and post-translational modifications may be used; e.g., mammalian, insect, yeast or plant expression systems.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted SCPF coding sequence.

In bacterial systems a number of expression vectors may be advantageously selected depending upon the use intended for the SCPF expressed. For example, when large quantities of SCPF are to be produced, vectors which direct the expression of high levels of fusion protein products that are readily purified may be desirable. Those which are engineered to contain a cleavage site to aid in recovering SCPF are preferred. Such vectors include but are not limited to the *E. coli* expression vector pUR278 (Ruther et al., 1983, EMBO J. 2:1791), in which the SCPF coding sequence may be ligated into the vector in frame with the lac Z coding region so that a hybrid SCPF-lac Z protein is produced; pIN vectors (Inouye & Inouye, 1985, Nucleic acids Res. 13:3101–3109; Van Heeke & Schuster, 1989, J. Biol. Chem. 264:5503–5509); and the like.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

In cases where plant expression vectors are used, the expression of the SCPF coding sequence may be driven by any of a number of promoters. For example, viral promoters such as the 35S RNA and 19S RNA promoters of CaMV (Brisson et al., 1984, Nature 310:511–514), or the coat protein promoter to TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electropotation, etc. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

An alternative expression system which could be used to express SCPF is an insect system. In one such system, *Autographa californica* nuclear polyhedrosis virus (AcNPV) is used as a vector to express foreign genes. The virus grows in *Spodoptera frugiperda* cells. The SCPF coding sequence may be cloned into non-essential regions (for example the polyhedrin gene) of the virus and placed under control of an AcNPV promoter (for example the polyhedrin promoter). Successful insertion of the SCPF coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:584; Smith, U.S. Pat. No. 4,215,051).

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, secretion of the gene product may be used as host cells for the expression of SCPF. Mammalian cell lines may be preferable. Such host cell lines may include but are not limited to CHO, VERO, BHK, HeLa, COS, MDCK, −293, and WI38.

Mammalian cell systems which utilize recombinant viruses or viral elements to direct expression may be engineered. For example, when using adenovirus expression vectors, the SCPF coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the SCPF protein in infected hosts (e.g., see Logan & Shenk, 1984, Proc. Natl. Acad. Sci. USA 81: 3655–3659). Alternatively, the vaccinia virus 7.5K promoter may be used. (e.g., see, Mackett et al., 1982, Proc. Natl. Acad. Sci. USA 79: 7415–7419; Mackett et al., 1984, J. Virol. 49: 857–864; Panicali et al., 1982, Proc. Natl. Acad. Sci. USA 79: 4927–4931). Of particular interest are vectors based on bovine papilloma virus which have the ability to replicate as extrachromosomal elements (Sarver, et al., 1981, Mol. Cell. Biol. 1: 486). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neogene. Alternatively, the retroviral genome can be modified for use as a vector capable of introducing and directing the expression of the SCPF gene in host cells (Cone & Mulligan, 1984, Proc. Natl. Acad. Sci. USA 81:6349–6353). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the SCPF cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including but not limited to the herpes simplex virus thymidine kinase (Wiglet, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in tk$^-$, hgprt$^-$ or aprt$^-$ cells respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072; neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.5. Production of SCPF

The present invention relates to SCPF of both membrane bound and secreted forms. SCPF is naturally secreted by the 751 and ML-1 cell lines. SCPF can be isolated from the conditioned media of continuous cell lines and purified to homogeneity using a variety of protein purification procedures. Alternatively, SCPF may be produced by recombinant DNA techniques, or by chemical synthesis methods.

5.5.1. Purification of SCPF

SCPF may be purified from culture supernatants of cells that secrete it; i.e., either the cell line or genetically engineered recombinant host cell expression systems. In a specific embodiment, by way of examples infra, conditioned medium of 751 cell line is collected and SCPF purified by SDS-preparative gel electrophoresis. Alternatively, 751 or ML-1 cell lysate may be used as the source for SCPF. SCPF may also be purified by immunoaffinity methods using an anti-SCPF antibody. In addition, SCPF may be purified using isoelectric focusing methods.

Methods for purifying SCPF from crude culture media of cells may be adapted for purification of the cloned, expressed product. In addition, where the SCPF coding sequence is engineered to encode a clearable fusion protein, the purification of SCPF may be readily accomplished using affinity purification techniques. For example, a protease factor Xa cleavage recognition sequence can be engineered between the carboxyl terminus of SCPF and a maltose binding protein. The resulting fusion protein can be readily purified using a column conjugated with amylose to which the maltose binding protein binds. The SCPF fusion protein is then eluted from the column with maltose containing buffer followed by treatment with Factor Xa. The cleaved SCPF is further purified by passage through a second amylose column to remove the maltose binding protein (New England Biolabs, Beverly, Mass.). Using this aspect of the invention, any cleavage site or enzyme cleavage substrate may be engineered between the SCPF sequence and a second peptide or protein that has a binding partner which could be used for purification, e.g., any antigen for which an immunoaffinity column can be prepared.

Procedures which may be used to isolate the SCPF of the invention include those commonly used for the separation of protein substances including, for example, treatment of a sample containing SCPF with common precipitants for proteins, followed by fractionation techniques such as ion exchange chromatography, affinity chromatography, ultrafiltration and various combinations thereof. SCPF can be purified from a cell suspension by methods described in U.S. Pat. Nos. 4,885,236 and 4,882,268, for example. Other methods for purification of the polypeptide of the invention will be known to those of skill in the art (see, for example, *Current Protocols in Immunology*, Coligan, et al., eds. 1992, incorporated herein by reference).

The SCPF containing fractions can be subjected to SDS-PAGE under suitable conditions and the gel slice containing SCPF activity or corresponding to the molecular weight of SCPF is recovered. SDS-PAGE is performed according to the method of Laemmli, et at., (*Nature*, 227:680, 1970). Variations in conditions which are within a suitable range are understood to be encompassed within the purification procedure.

SCPF-containing fractions from SDS-PAGE can be isolated and further subjected to two-dimensional gel electrophoresis according to the method of O'Farrell (*J. Biol. Chem.* 250:4007, 1975). First dimension isoelectric focusing gels are run by standard methods using broad range ampholytes to resolve proteins with pI values between about 3.8 to about 8.0. Ampholyte solutions from pH 2–11 are added in varying amounts depending on the pI of the protein of interest. If broad increased resolution in a narrow pH is desired, narrow range ampholytes can be added to broad range ampholytes in a 2:1 ratio. Preferably, SCPF and its corresponding isoforms are resolved using ampholytes which separate proteins with pI of about 5 to about 9, and more specifically from about 7 to about 8. Second dimension gels are generally run as 10–20% acrylamide gels, however, any conventional slab gel can be used.

Proteins resolved by two-dimensional gel electrophoresis can be detected by standard methods such as Coomassie Blue and silver staining. Alternatively, proteins in a gel may be electrophoretically transferred to a blot transfer membrane and detected by staining with India ink or colloidal gold, or by western blotting. Preferably, the SCPF of the invention is detected by western blotting using the antibody of the invention.

The SCPF containing fractions can also be subjected to reverse phase HPLC and eluted with acetonitrile, for example. The SCPF which is obtained is substantially pure to permit N-terminal amino acid sequencing. The solution is dried under vacuum and redissolved in a small volume of acetonitrile 95%+TFA (0.08%). The concentrated sample is then introduced in a sequencer connected to a phenylthiohydantoine (PTH) analyzer.

The biological activity of a gel purified cytokine, such as the SCPF of the invention can be tested in bioassays for stimulation (and/or inhibition) of proliferation of an indicator cell line. For example, SCPF activity can be assayed in ML-1, KG-1a, or partially purified $CD34^+$ bone marrow cells.

5.5.2. Chemical Synthetic Methods

The SCPF molecule may also be produced in whole or in part by solid phase chemical synthetic techniques based on its amino acid sequence. (See Creighton, 1983, Proteins Structures and Molecular Principles, W. H. Freeman and Co., N.Y. pp. 50–60; Stewart and Young, 1984, Peptide Synthesis, 2nd ed., Pierce Chemical Co.). This approach may be particularly useful in generating segments of SCPF corresponding to one or more of its biologically active regions.

5.6. Anti-SCPF Antibody Production

Also within the scope of the invention is the production of polyclonal and monoclonal antibodies which recognize SCPF or related proteins.

Various procedures known in the art may be used for the production of polyclonal antibodies to epitopes of SCPF. For the production of antibodies, various host animals can be immunized by injection with the SCPF protein, or an SCPF peptide, including but not limited to rabbits, hamsters, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

In a specific embodiment of the invention, gel purified SCPF was used to immunize rabbits for the generation of SCPF-specific antibodies. One such antiserum (SAM.1) was demonstrated to contain antibodies that specifically reacted with SCPF and thereby, inhibited its activity on stimulating the growth of 751 cells in an autocrine fashion. See Section 7.2.2., infra.

A monoclonal antibody to an epitope of SCPF may be prepared by using any technique which provides for the production of antibody molecules by continuous cell lines in culture. These include but are not limited to the hybridoma technique originally described by Kohler and Milstein (1975, Nature 256, 495–497), and the more recent human B-cell hybridoma technique (Kosbor et al., 1983, Immunology Today 4:72; Cote et al., 1983, Proc. Natl. Acad. Sci. 80:2026–2030) and the EBV-hybridoma technique (Cole et al., 1985, Monoclonal Antibodies and Cancer Therapy, Alan R. Liss, Inc., pp. 77–96). Techniques developed for the production of "chimeric antibodies" by splicing the genes from a mouse antibody molecule of appropriate antigen specificity together with genes from a human antibody molecule can be used (e.g., Morrison et al., 1984, Proc. Natl. Acad. Sci., 81:6851–6855; Neuberger et al., 1984, Nature, 312:604–608; Takeda et al., 1985, Nature 314:452–454). In addition, techinques described for the production of single chain antibodies (U.S. Pat. No. 4,946,778) can be adapted to produce single chain antibodies.

Antibody fragments which contain the binding site of the molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Antibodies to SCPF may find use in the qualitative and quantitative detection of membrane bound or secreted SCPF in mature, precursor and subcomponent forms, in the affinity purification of SCPF protein, in the elucidation of SCPF biosynthesis, metabolism and function, and in the screening of SCPF expression libraries for gene sequences that encode immunogenic epitopes. Antibodies to SCPF may also be useful as diagnostic and therapeutic agents for germ cell or other tumors.

5.7. Uses of SCPF

The functional activities and target cell specificity of SCPF provide for a wide variety of uses in vitro and in vivo. Any compound which includes SCPF, or fragments and derivatives thereof which exhibit growth stimulatory activity, either alone or in conjunction with other biologically active growth factors, inhibitors, or immunomodulatory agents, may be employed in the practice and method of the invention. SCPF, SCPF-related molecules and compositions thereof may be especially useful in augmenting the proliferation of germ/stem cells including but not limited to hematopoietic stem cells.

A major impediment in the current attempts to achieve stable integration of exogenous genes in hematopoietic stem cells is the inability of the known cytokines to stimulate such cells to proliferate without differentiation. SCPF has been shown to be capable of inducing purified $CD34^+$ cells to enter the cell cycle and proliferate in long term culture (Section 7.2.5., infra). The SCPF may be used to facilitate genetic manipulation of stem cells for use in gene therapy of hematologic disorders including but not limited to sickle cell anemia.

The findings that SCPF is an autocrine growth factor and that it also acts on cells of the hematopoietic lineages imply that SCPF may be a cytokine specific for primitive germ/stem cells of different tissue origins. It has been shown that stem cell populations exist in a variety of organs and tissues including the brain, liver and skin. Further, hair loss has also been linked to a defect in stem cell proliferation surrounding hair follicles. Therefore, SCPF may be a useful agent for treatment of conditions that require the growth of stem cell populations irrespective of their tissue of origin including but not limited to hair loss.

In addition, cells expressing the SCPF receptor may be detected by using labeled-SCPF or SCPF-related molecules in a receptor binding assay, or by the use of antibodies directed to the SCPF receptor itself. Cells may be distinguished in accordance with the presence and density of receptors for SCPF, thereby providing a means for predicting responsiveness of such cells to the biological activities of SCPF.

5.8. Method for Identification of Cytokines from Germ Cells

The present invention illustrates a novel approach to the identification and isolation of growth factors or cytokines having biologic activities on a variety of germ/stem cells. Any germ cell tumors can be obtained from surgical materials and prepared for in vitro culture for the practice of the invention. The cell lines may be selected based on expression of certain markers or responses to certain growth factors, and both adherent and non-adherent cell populations may be maintained. Tissue lineage characterization of the established cell lines can be determined by flow cytometry analysis using antibodies to various cell surface and internal cytoskeletal elements including the leukocyte antigens and intermediate filaments. Further, expression of oncogenes including c-myc, c-fms, c-ras, c-myb, c-fos, c-src, c-erb, c-neu, c-ros, and c-sis can be examined by the use of molecular probes.

In order to identify new cytokines produced by the established cell lines, cells may be metabolically labeled and secreted proteins analyzed by SDS-PAGE. Alternatively, culture supernatants may be directly analyzed by applying them to various cell types used as indicators which are known to respond to specific cytokines in bioassays. Having identified a major protein by SDS-PAGE and/or by biologic activity, the protein may be purified by SDS-preparative gels, ion exchange chromatography, and isoelectric focusing gels (See Section 5.5.1., infra). Purity of the proteins can be verified by SDS-PAGE, quantified by protein assays, their activities confirmed in bioassays, and used as immunogens for the production of polyclonal and monoclonal antibodies.

The purified proteins can be further tested in bioassays to stimulate and/or inhibit proliferation of a variety of indicator cell lines of diverse tissue types. Radiolabeled proteins may also be used to identify their cell surface receptors by methods such as affinity labelling. Specific antibodies to the cytokines may be used to identify and quantify membrane forms and secreted forms of the cytokines, to study their biosynthetic pathways, to affinity purify the proteins and to immunoscreen expression libraries for the molecular cloning of the coding sequences using, for example, the approaches and techniques described supra.

6. EXAMPLE: GENERATION OF 751 CELL LINE LINE THAT PRODUCES SCPF

The sections below describe the 751 cell line which was discovered in the course of establishing a germ cell tumor line. The growth of the 751 cell line is regulated by one or more growth factors heretofore undescribed.

6.1. Materials and Methods 6.1.1. Cell Cultures

The 751 cell lines were maintained in RPMI 1640 supplemented with 10% fetal bovine serum, L-glutamine, and antibiotics (penicillin/streptomycin). The viability and the cell concentration was assessed using trypan blue exclusion. The cell concentration was adjusted to give $1\times10^5$ cells/ml and seeded into 75 cm tissue culture flasks, then incubated at 37° C. in an atmosphere of 5% $CO_2$ in air.

6.1.2. Animals

The triple-immune-deficient by/mu/xid female mice (BNX mice) were obtained from Harlan Sprague Dawley Inc., Ind., and maintained in germ-free animal colonies. The mice were fed sterile Rodent Blox and acidified water ad libtium, and used in experiments when 7–9 weeks old.

6.1.3. In Vitro Cell Growth Kinetics

The in vitro growth kinetics of the 751 cell lines were carried out as follows. The initial growth curve studies were set up to obtain optimal starting cell concentration. The initial growth curves, therefore, were run at $5\times10^3$, $5\times10^4$, and $1\times10^5$ cells/well. Cell counts were performed at 12-hour intervals for 7 days. All cell counts/sample were carried out in triplicate. These preliminary studies revealed that the optimum cell number for all the subsequent growth curves was $5\times10^4$. The 751 cells were then plated in 12 well plates to give a final concentration (in 2 ml volumes) of $5\times10^4$/well. All counts were performed at 12-hour intervals for 7 days and the percentage viability was also recorded. All cell counts/sample were carried out in triplicate.

6.1.4. In Vivo Cell Growth Kinetics

The ability of the 751 cell line to transplant into the BNX mice was tested. To determine the rate of tumor growth, $Log_{10}$ serial dilutions fo 751-NA cell line was inoculated (0.1 ml) subcutaneously over the hindquarters of the BNX mice. Eight mice per dilution were used. Inoculated mice were examined twice a week for the appearance of tumors. Once tumors were evident, the tumor size was measured, every two days, using calipers. Tumor measurements were taken by measuring two perpendicular diameters and the tumor area estimated by multiplying the two values together.

6.1.5. Flow Cytometric Analysis 751 or ML-1 cells were screened with monoclonal antibodies that were specific for leukocyte cell surface markers: CD2, CD3, CD4, CD5, CD7, CD8, CD10, CD14, CD19, CD20, CD33, CD34, CD38, CD56, HLA Class I and Class II. These antibodies were made available by Becton Dickinson, Calif. The flow cytometric analysis was performed as follows (Griebel et al., 1988). The 751 tumor cells were centifuged (1,000 rpm for 10 minutes) and resuspended at a concentration of $2\times10^7$ in 0.1M PBS containing 0.2% gelatin, 1 mM sodium azide and 2% normal rabbit serum. Fifty microliters of the cell suspension was added to 50 µl of the appropriate monoclonal antibody in a 96-well flat-bottomed microtiter plate and incubated for 30 minutes at 4° C. The cells were then washed three times with ice-cold PBS-gelatin and incubated for a further 30 minutes at 4° C. with 100 µl of FITC-labelled F(ab)'2 goat antimouse immunoglobulin (heavy and light chain specific) (Cooper Biomedical, Malvern, Pa.) diluted 1/75 with PBS-gelatin. Cell aggregates were removed from all samples by prefilteration through a 2-millimicron. Nylon monofilament mesh immediately prior to FACS analysis (Small Parts Inc., Miami, Fla.). Appropriate controls were included to detect non-specific labelling. In these controls, the bone marrow was reacted with either FITC labelled F(ab)'2 alone or with an isotype matched monoclonal antibody specific for an irrelevant antigen. The FITC-labelled 751 tumor cells were analyzed using a Becton Dickinson Fac-Scan flow cytometer. Data from 20,000 cells were collected to analyze the patterns of monoclonal antibody reactivity. Two parameter analysis of forward angle light scatter (FALS) versus 90% light scatter (LI90) was used to eliminate blots of FALS versus fluorescence and as histograms of fluorescence versus cell numbre. The data were also given as % of cells positive for a given phenotype marker.

Antibodies to various antigens were purchased from commercial sources: anti-cytokeratin, anti-NF200, anti-NF160, anti-NF68 (Sigma, St. Louis, Mo.); anti-vimentin (Boeringer Mannheim); anti-GFAP and anti-NSE (Dakopatts, Glostrup, Denmark). FITC-conjugated secondary antibody reagents were purchased from Sigma.

6.2. Results

6.2.1. Case History

In 1989, a 19-year old white female presented to her local physician complaints of headaches and double vision. She was diagnosed by CT scan as having a large suprasellar mass. The mass was surgically debulked and a ventriculoperitoneal (VP) shunt was put in place. Postoperative local radiation was administered with a total dose of 5000 cGy. She was apparently in good health, with control of residual tumor, until one year later, when she again presented with complaints of headaches. She was also found to have multiple subcutaneous masses along, the VP shunt. Physical examination revealed a mass on the right side of her skull near the VP shunt, and two masses on her chest wall along, the shunt tubing. CT scan of her head revealed local recurrence and a soft tissue mass near her shunt. Furthermore, metastatic deposits in her abdomen were also found. The lesion on the skull was aspirated; cytology of cells from this area was consistent with a germ cell tumor. In February of 1990, to further define the histology, one of the chest-wall masses was resected. Histological examination of the tumor revealed non-germinomatous mixed germ cell tumor similar to the original biopsy taken in 1989, with a prominent population of small primitive cells.

6.2.2. Origin of 751 Cell Lines

At the time of surgery in February 1990, a small portion of tumor from the chest wall was sent to the laboratory for cell isolation and in vitro growth in cell culture. The tumor was divided into approximately 3 mm portions. The minced tumor was subjected to limited digestion using versene-trypsin at 37° C. for 10 minutes. After enzyme treatment, the non-digested tissue was removed by sedimentation, and the supernatant fluid collected, centrifuged, and the cell pellet harvested. The cell pellet was resuspended and cultured in growth medium.

Primary cultures were examined daily and media changed weekly. The original cell cultures contained cells which were both adherent and non-adherent to the plastic dishes. Over the next two months, the number of morphologically distinct cell types diminished to the point where there only appeared to be two defined populations replicating as a co-culture, one which grew as an adherent cell, the other as a non-adherent cell. Approximately 16 weeks into the culture of this germ cell line, the non-adherent cell outgrew the adherent population and became a predominant cell type cloned by limiting dilution and designated 751-NA. Surprisingly, 751-NA was found to be a murine cell line as determined by karyotype analysis and its expression of murine isoforms of various cellular enzymes. The 751-NA has been maintained in in vitro culture in stable form using the aforementioned growth medium through multiple-cell-population passages. To develop the murine tumor model from the 751-NA cell line, cells were injected into the subcutaneous tissues of the beige, nude, x-linked immunodeficient (BNX) mouse and germ cell tumors allowed to develop, similar in histologic appearance to the original patient's tumor. Tumors from the BNX-mouse subcutaneous site were aseptically removed, treated with versene trypsin, supra, and a new non-adherent cell line reestablished in in vitro culture; designated 751-MU. Two further cell lines which were taken from metastatic deposits in the liver and drainage lymph node were established, designated 751-LIV and 751-LN, respectively.

6.2.3. Characterization of the 751 Cell Lines

The characterization of the established 751 cell lines examined both growth kinetics and phenotype. In vitro growth was examined using growth curve analysis and showed unique growth pattern with little or no lag phase, but logarithmic growth initially, a short stationary phase, then dramatic decline in viability. The rapidity of growth is illustrated by the calculated doubling time during the log phase of 7-to-8 hours.

The growth of the cell lines in vivo was assessed using a BNX murine model. To determine the rate of growth of the cells when injected into the mouse, serial log dilutions of the various 751 cell lines were inoculated into the subcutaneous tissue of the hindquarters. The mice were examined twice weekly and tumor measured in two perpendicular diameters. It was found that tumors arose from inocula as small as 100 cells with tumor evident at 20 days post-inoculation. Inoculation of $1 \times 10^3$ cells gave rise to tumors in only seven days rather than 2–3 months, as most reported murine tumor models have found. In addition, most reported tumors do not grow with inocula of less than $5 \times 10^5$ cells.

To determine the origin of this cell population (751-NA, 751-LIV, 751-LN) cells were analyzed by flow cytometry using both polyclonal and monoclonal antibodies directed against specific cell determinants for neuro-ectodermal germ cells, neuronal lineages, and glial cell lineages. The following antibodies were used to complete this study: Placental Alkaline Phosphatase (PAP) and Human Chorionic Gonadotropin (XCG) were used as markers to detect germ cells of non-neuronal cells; Cytokeratin (anti-human or anti-rat) and Vimentin (anti-human) were used as markers for germ cells of neuro-ectodermal origin; Glial Fibrally Acidic Protein (GFAP) as a marker for glial lineage; and Neural Specific Enolase (NSE), and Neural Filament Protein (NFP) —68,150,&200 as markers for cells of neuronal lineage. Results indicate that the cell populations (751-NA, 751-MU, 751-LN) represent a primitive brain germ cell which could, under the appropriate conditions, form cells of either neuronal or glial lineage (see, FIG. 1).

Further flow cytometry phenotyping of 751 cells indicated the following mean percentage of positively fluorescent cells (in parentheses) with the corresponding antibody: anti-rat cytokeratin 8 (0.86); anti-rat cytokeratin 19 (0.40); anti-human vimentin (1.29); mouse anti-human monoclonal NF-68 (33.16); rabbit anti-human polyclonal NF-150 (64.54); mouse anti-human monoclonal NF160 (8.50); mouse anti-human monoclonal NF-200 (61.13); HPAP (56.28); rabbit anti-human polyclonal GFAP (67.69); rabbit anti-human polyclonal NSE (78.34); and goat anti-human HCG (50.04).

Initial studies were designed to ascertain whether the 751-cell line expressed any known human leukocyte markers, including the HPCA-1 (CD34). FACS analysis of the 751 cell line for expression of CD45, CD19, CD20, CD3, CD4, CD8, CD2, CD5, CD7, CD10, CD14, CD71, and CD34 shows that this primitive cell line is devoid of all leukocyte markers including the CD34 marker. However, subsequent karyotype analysis revealed that 751 cells are murine. Thus, the SCPF produced by the 751 cells is presumed to be murine in origin. Surprisingly, the "murine" SCPF has biological activity on human target cells.

6.2.4. Oncogene Expression by 751 Cell Lines

The role of proto-oncogenes in the malignant phenotype expression of cells (both in vitro and in vivo) has been investigated in many cell culture systems. Using DNA probes to a number of different oncogenes, Northern analysis was performed. These analyses showed that 751 cells contain abundant mRNA's for the oncogene c-myc as well as oncogene receptor c-fms. This is especially significant, as the c-fms oncogene serves as receptor for macrophage-colony stimulating factor (M-CSF). While the M-CSF receptor has been described on microglia in the brain, its presence on primitive cells of neural origin has not been reported. It is, however, found on progenitor cells in the bone marrow and is one of the growth factors involved in lineage-specific differentiation of monocyte/macrophage cells. The expression of this receptor indicates a role of M-CSF in the proliferation and differentiation of primitive germ cells.

7. EXAMPLE: STEM CELL PROLIFERATION FACTOR DERIVED FROM THE 751 CELL LINE

The experiments described below demonstrate that SCPF is 32 kDa when secreted and 37 kDa when cell bound. Two-dimensional gel electrophoresis of the purified protein indicates the existence of multiple isoforms of the protein with PIs ranging from about 7.0 to 8.0.

7.1. Materials and Methods

7.1.1. Radiolabelling and Polyacrylamide Gel Electrophoresis

The 751 cell line was grown in Dulbecco's Minimal Essential Medium (DMEM) supplemented with 10% fetal bovine serum and antibiotics (Penicillin/Streptomycin) to a density of $10^6$ cells/m. in a 30 ml culture flask. Once the required density was reached, the cells were washed free of the growth medium and were recultured in 75% methionine-free DMEM supplemented with 25% DMEM containing methionine and 2% of [$^{35}$S]-Methionine (Amersham, Ill.) and re-incubated. At 24-hour intervals, the supernatants were harvested, configured to remove non-adherent cells, and stored at −20° C. The $^{35}$S-labelled supernatants were then added to sample buffer (Tris-HCl, 2-mercaptoethanol, 10% glycerol, 2% SDS, and 0.001% bromophenol blue) and heated at 100° C. for 5 minutes. The samples were then applied to SDS-PAGE and electrophoresed as previously described. Following electrophoresis, the gel was fixed in TCA (10%, w/v); glacial acetic acid (10% v/v) and methanol (30% v/v). After fixation the gels were soaked in Fluorohance™ (Research Products Inc., Prospect Ill.) for a further 30 minutes. The gel was removed, placed upon fiber paper (pre-wet) and dried under a vacuum with heat (60° C.). Following drying, the gel was exposed to high speed x-ray field (Kodak X-omat AR) and stored at −70 for 24–48 hours after which time the autoradiographs were developed and analyzed.

Cell lysates, purified proteins and supernatants from the 751-cell lines were solubilized in electrophoresis buffer and analyzed on 12% SDS-polyacrylamide gels using the discontinuous buffer system of Laemmeli (1970). Unless otherwise stated, the electrophoresis was performed under denaturing conditions. In each experiment, molecular weight markers (Bio Rad Laboratories,) were electrophoresed in parallel and visualized by staining with Coomassie Blue.

7.1.2. Gel Purification of SCPF

Serum-free supernatants were harvested from 751-NA cells 48 hours post culture. The supernatants were concentrated 20-fold using a Savant concentration and then dialyzed. The concentrated sample was then applied to a 12% preparative SDS-PAGE. Following the SDS gel electrophoresis, the gels were subjected to negative staining with 0.3M $CuCl_2$. The protein band of interest was removed from the gel, cut into small fragments, and placed in a dialysis bag (12–14,000 molecular weight cut-off) with 200 µl of elution buffer (g 25 mM Tris-Glycine, pH 8.3). The sample was then electro-eluted at 100 V for 18 hours at 4° C. Following electroelution the current was reversed for 30–40 seconds, the dialysis bag removed, and the sample harvested and dialyzed overnight. All elutriation preparations were checked for purity by SDS-PAGE prior to use as an immunogen or for use in cell proliferation assyas.

7.1.3. Preparation of Anti-SCPF Antibody

New Zealand white rabbits were bled prior to immunization and the pre-immune sera used to establish base lines. Rabbits were immunized subcutaneously with 7 µg of purified SCPF polypeptide from cell line 751 containing Ribi adjuvant. Two weeks following the initial injection, the rabbits were given a second injection containing polypeptide and Ribi adjuvant. The rabbits received a minimum of 5 subcutaneous inoculations with the immunogen plus Ribi adjuvant. The rabbits were bled at each of the innoculation time points and the serum tested by Western Blot for the presence of antibody reactive to the 32 kDa proteins. All sera containing high concentrations of antibody specific for the 32 kDa protein were aliquoted and stored at −70° C.

7.1.4. Western Immunoblotting

Cell lysates from the 751-NA tumor cell line were prepared in electrophoresis buffer and the proteins resolved using SDS-polyacrylamide gel electrophoresis (Laemmeli, 1970). Proteins present in the gels were transferred to nitrocellulose based upon the technique described by Towbin et al., 1979, using the Bio-Rad Semi-Dry Transblot Apparatus. The gel was equilibrated in electroblot buffer (25 mM) Tris (192 mM) glycine and (5% v/v) methanol at pH 8.3. The nitrocellulose membrane was also equilibrated in this buffer. Following equilibrium, the nitrocellulose membrane was positioned upon the filter paper on the platinum anode, and the gel was then layered on top and followed by presoaked filter paper. After positioning the cathode, the sample was blotted/electrophoresed at 25 volts for 35–40 minutes. Following transfer, the membrane/blot was washed four times in phosphate buffered saline containing gelatin and Tween 20 (PBS-gel-tween). The blots were incubated overnight with the rabbit-polyclonal antibody, previously diluted in PBS-Tween. Following incubation, the blots were washed four times in PBS-Gel-Tween and then incubated with peroxidase labeled goat anti rabbit (Sigma, St. Louis, Mo.) for one hour and then washed twice in PBS-Tween and then twice in PBS alone. Substrate (0.05% (w/v) 4 chloro-1-naphthol and 30% $H_2O_2$) was added and the blot incubated in the dark at room temperature for 60 minutes. Positive reactions were indicated by the appearance of dark blue bands.

7.1.5. Clonogenic Assays 751-tumor line is capable of forming colonies (>than 128 cells/colony) in methyl cellulose containing DMEM supplemented with 10% FBS. $10^3$ cells were added to 1.0 ml of methyl cellulose, to this was also added varying dilutions of the polyclonal rabbit antibody to the 32 kDa protein in a volume of 100 µl. The sample was well mixed and plated in 20 mm petri dishes and inoculated at 37° C. in an atmosphere of 5% $CO_2$ in air. At 48 hours post-culture, the number of colonies was enumerated using an inverted light microscope.

Antibodies specific for various colony-stimulating factors were purchased from Genzyme (Boston, Mass.)

7.1.6. Long-Term Cultures (Gordon-Type Cultures)

In order to grow human hematopoietic stem cells in long-term in vitro culture, adherent cell populations are required to provide soluble and cell contact-dependent factors. Human marrow aspirates were collected in medium containing preservative-free heparin and diluted in long-term culture medium to give a final volume of 8 ml containing $2 \times 10^7$ nucleated cells in a 25 cm$^2$ tissue culture flask (Gordon et al., 1987, Exp. Hematol. 15:772). The growth medium consists of α-MEM supplemented with inositol (40 mg ml$^{-1}$), folic acid (10 mg ml$^{-1}$), hydrocortisone ($10^{-6}$M), 2-mercaptoethanol ($2 \times 10^{-4}$M), and a 1:1 mixtures of horse serum and FBS to give a final serum concentration of 25%. To facilitate attachment, the cultures were placed at 37° C. After 4 days, the medium and non-adherent cells were collected, centrifuged over Ficoll/Hypaque to remove granulocytes and red cells, and the light density fraction returned to the culture flask. Thereafter, half of the growth medium and non-adherent cells were replaced at weekly intervals with fresh medium until a confluent adherent monolayer forms.

Medium and non-adherent cells were removed from the long-term cultures and 2 ml of fresh medium added. The flasks were then irradiated at 2000 rad to eliminate hematopoietic cells present within the adherent layer. Following irradiation, the medium was removed and replaced with 8 ml fresh medium containing the purified cell populations to determine whether they would reconstitute and initiate myelopoiesis in the cultures. As controls, some long-term cultures were reconstituted with medium only to demonstrate that the irradiation was sufficient to eliminate all hemetopoietic progenitors (negative control). In addition, some long-term cultures were reconstituted with normal bone marrow cells (positive control). Following reconstitution, half of the medium and non-adherent cells were collected weekly, counted, and plated in methylcellulose cultures containing growth factors. In addition, at certain time points, a culture flask was sacrificed and the adherent cells subjected to trypsinization to obtain a single cell suspension for hematopoietic colony assay.

7.1.7. In Vitro Progenitor Cell Assays

The following assays were the standard protocols used to measure CFU activity of cells.

The pre-colony-forming unit (Pre-CFU) assay was designed to detect early hematopoietic progenitors in human marrow (Smith et al., 1991, Blood, 77:2122). The isolated cells were incubated with rIL-1α (100 U ml$^{-1}$) and rIL-3 (50 ng ML$^{-1}$), harvested and enumerated seven days post-culture. 1×10$^5$ cells plated with 1000 U ml$^{-1}$ of recombinant GM-CSF in 0.36% agarose and colonies (>50 cells) were scored 14 days after incubation.

To detect the myelomonocytic/erythroid precursor cells (CFU-GEMM) and the progenitor cells for the erythroid series (BFU-E), a combined CFU-GEMM/BFU-E assay was used (Ash et al., 1981, Blood 58: 309). Briefly, 1×10$^5$ purified stem cells were plated in 35 mm diameter plates in a total volume of 1.0 ml of Iscove's modified Dulbecco's medium supplemented with 5×10$^5$M 2-mercaptoethanol, 30% FBS, 100 U ml$^{-1}$ of human rIL-3 and 1.0 U ml$^{-1}$ of Epo and 0.9% methyl cellulose. The cultures were incubated for 14 days at 37° C. in a humidified atmosphere containing 5% $CO_2$ and 10% $O_2$ in air. Colonies (>50 cells) were enumerated using an inverted microscope.

Early hematopoietic progenitors representative of CFU-GM were also detected (Iscove et al., 1971, Blood 37:1). Briefly, 1×10$^5$ purified stem cells were plated in 35 mm diameter petri dishes in a final volume of 1.0 ml α-MEM supplemented with 2% FBS, 0.6% L-glutamine, 0.9% methyl cellulose and 100 U ml$^{-1}$ of human recombinant rIL-3. The cultures were incubated as described for CFU-GEMM assays and colonies enumerated using an inverted microscope.

7.2. Results

7.2.1. Biochemical Identification of SCPF

To visualize proteins secreted by the 751 cell line, pulse chase experiments were performed using [$^{35}$S]-methionine. Cells were labelled for 12 hours in methionine-free media, after which time they were placed in cold growth media containing methionine. The $^{35}$S-labelled supernatant was then subjected to SDS-PAGE. One major protein was found to be secreted from the 751 tumor cells, the calculated apparent molecular weight (by regression analysis) was shown to be 32 kDa. Furthermore, maximum secretion of this protein was found to occur at 24–36 hours post-culture (FIG. 2).

Isolation of this protein was achieved by resolution of the secreted polypeptides by SDS-PAGE and identification of the 32 kDa polypeptide by migration relative to molecular weight markers. Once identified, proteins were transferred by electroblotting onto nitrocellulose and the region corresponding to the 32 kDa protein cut out and dissolved in dimethyl sulfoxide (DMSO). This was inoculated into rabbits for the generation of a polyclonal antibody generated.

The specificity of the antibody was tested against whole cell lysates from 751-LN using a western immunoblotting technique. In this system, the proteins were transferred to nitrocellulose using the Bio-Rad semi-dry transfer apparatus and then subjected to a modified colorimetric ELISA. Positive band(s) reactions were indicated by the appearance of dark blue bands. These assays showed a polyclonal antibody that reacts specifically with a single protein of an apparent molecular weight (calculated by regression analysis) of 37 kDa (FIG. 3). This, in conjunction with the molecular weight of the secreted protein (32 kDa) suggests that: (1) a signal sequence exists to transport the secreted protein to the cell surface; (2) a transmembrane component to the molecule anchors the protein to the membrane; and (3) two forms of this protein exist, one a membrane-bound species (37 kDa) and the other a soluble extracellular species of 32 kDa molecular weight. Both forms may act as a "growth factor" with the membrane-bound form additionally involved in cell-cell interactions during normal germ cell development.

7.2.2. Autocrine Growth Regulation of Germ Cell Tumor Line by SCPF

Using the polyclonal antibody derived against the 32 kDa protein produced by cell line 751, colony inhibition assays in methyl cellulose were conducted. In previous experiments, 751 cells were shown to form colonies of >50 cells in 48 hours in methyl cellulose. If the 32 kDa protein was an autocrine factor regulating the growth of tumor cells, blocking the binding of the protein to its cellular receptor should decrease cell replication and growth of the colonies. Using serial dilutions of the rabbit polyclonal anti-32 kDa antibody, 751-NA, 751-MU, and 751-LN tumor cells were mixed into methyl cellulose containing various serum dilutions, incubated at 37° C. for 48 hours, then newly-formed colonies counted. At a reciprocal dilution of, 1/20, the antibody inhibited 98% of colony formation. This inhibition was shown to be antibody concentration-dependant, with significant inhibition (>25%) occurring at serum dilutions of 1/120. Normal rabbit serum at a 1/20 dilution did not block colony formation (FIG. 4). Furthermore, the ability of the anti-37 kDa antibody to block cell proliferation was tested in $^3$H-thymidine uptake assays (FIG. 5). This figure shows that the antibody does in fact inhibit cell proliferation and that this inhibition is specific for germ/stem cells, since only the 75I-Mu Met and the BO Bm.1 cells were inhibited. The A251 neuroblastoma cell line was not inhibited.

7.2.3. Interaction of SCPF with Human Bone Marrow Cell Populations

The experimental results described below indicate that the anti-SCPF antibody (SAM.1) specifically interacts with a small population of bone marrow cells and furthermore, this population appears to fall within the CD34$^+$ compartment. Finally, the anti-SCPF recognizes a marker distinct from the CD34 protein and may be important in the delineation of a stem cell population.

Due to the primitive nature of the 751 cell and that it appears to be regulated by an autocrine growth factor (SCPF), the following experiments were designed to determine whether the purified native protein would interact with bone marrow cells. This interaction was analyzed using (1) bone marrow-methyl cellulose clonogenic assays; (2) $^3$H-thymidine incorporation assays; and (3) flow cytometry. FIG. 3 shows an SDS-PAGE-gel stained by Coomassie blue and a Western blot using SAM.1 polyclonal antibody of the purified native 37 kDa protein used in these assays. A single band was present on the gel migrating at 37 kDa (FIG. 3A). A nitrocellulose blot of this gel when reacted with SAM.1, antibody revealed a band in the same position (FIG. 3B). When the purified SCPF was used in clonogenic assays at varying concentrations (Table 1), no colonies of defined morphology were observed.

TABLE 1

Human Bone Marrow Clonogenic Activity of Stem Cell Proliferation Factor

| Stimulant | GM | G | M | BLAST | TOTAL |
|---|---|---|---|---|---|
| r human GM-CSF | | | | | |
| 50 u/ml | 26/31 | 70/59 | 11/15 | — | 107/105 |
| 10 u/ml | 14/20 | 52/41 | 6/5 | — | 72/66 |
| 1 u/ml | 5/3 | 6/1 | 1/0 | — | 12/4 |
| 751-conditioned media (× 10 Conc) | — | — | — | 9/7 | |
| 751-SCPF (native) 100 µg/m. | — | — | — | 16/15/19 | |
| 751-SCPF (native) 10 µg/ml | — | — | — | 11/13/9 | |

TABLE 1-continued

Human Bone Marrow Clonogenic Activity of Stem Cell Proliferation Factor

| Stimulant | GM | G | M | BLAST | TOTAL |
|---|---|---|---|---|---|
| 751-SCPF (native) 1 µg/ml | — | — | — | 6/8/7 | |
| Control - Media alone | — | 1 | — | — | 1 |

Assay:
Clonogenic (methyl cellulose)
In vitro 1 × 10⁴ Non-adherent cells/well
14-day assay However, blast-like cells in very loose clusters were observed in these assays. These blast-like cells were removed from the clonogenic assays—placed in suspension culture with and without stromal feeder layers and expanded using SCPF. The suspension without stromal feeder cells were harvested at 96 hours post-culture and subjected to flow cytometric analysis using the monoclonal antibody HPCA-1 (anti CD34) an isotype control was used as a negative control and W6/32 (anti-human HLA Class 1) monoclonal as a positive control. FIG. 6 is a flow cytometric analysis of these cells. All the cells stained with the W6/32 anti-HLA class I, furthermore a high percentage of the cells also reacted with anti-CD34. It was evident that not all the cells were CD34⁺. This may have been due to (1) removal of non CD34⁺ cells from the clonogenic assay prior to the expansion in suspension culture or (2) differentiation of cells while in the suspension culture. However, this was an indication that the SCPF protein interacted with cells of the CD34⁺ phenotype. Cells placed in the long-term cultures with stromal feeder layers (FIG. 7) were analyzed for continuous growth under Gordon-culture conditions.

FIG. 7 shows that these cells proliferated in long term Gordon-culture in the absence of SCPF. It appears that stromal cells were important for both soluble factors and that cell-cell contact in order to maintain good growth and viability. Cells given stromal conditioned media only did not proliferate or survive. Cells were removed at 72 hours from the Gordon cultures and tested for replating efficiency in the presence of recombinant GM-CSF (Table 2).

TABLE 2

Replicating Efficiency of SCPF Stimulated Bone Marrow Cells: Response to Human Recombinant GM-CSF

| Treatment/Culture | Conc (u/ml) | Colony Type (Morphology) | | | |
|---|---|---|---|---|---|
| | | G | GM | M | Total |
| Gordon cultures | 100 | 29 | 36 | 11 | 76 |
| human r-GM-CSF | 50 | 23 | 41 | 9 | 73 |
| | 25 | 14 | 27 | 8 | 46 |
| | 5 | 4 | 19 | 2 | 25 |
| | 1 | — | 11 | 2 | 13 |
| Medium alone | | 1 | 2 | 1 | 4 |

It appears that the cells induced in the colony assays, then expanded in Gordon-cultures, were able to respond to GM-CSF and form colonies of granulocytes (G), monocytes (M), and mixed GM cells, indicating, therefore, their ability to undergo lineage differentiation into myeloid cells. Proliferation of bone marrow cells, as measured by ³H-thymidine incorporation, also indicated that SCPF induced cells of bone marrow origin to proliferate (FIG. 8).

From the foregoing experiments, it is evident that SCPF interacts with a population(s) of bone marrow cells. Since a polyclonal rabbit antibody (SAM.1) had been produced against SCPF from cell line 751, and that SCPF was cell bound, flow cytometric analysis of bone marrow cells was carried out to ascertain the phenotypic nature of the cells in bone marrow that were interacting with SCPF. The ability of SAM.1 to recognize human bone marrow cells was tested using both adherent depleted human bone marrow cells and human cord blood as a source of newly hematopoietic stem cells. FIG. 9 shows that SAM.1 binds to a very small population, of cells within bone marrow (2.5%) and cord blood (1.96%). In an attempt to define this population, two-color FACS analysis was performed using an anti-CD34 phycoerythrin (PE) labelled antibody and the SAM.1 fluorescein isothiocyanate (FITC) system (FIG. 10). From these experiments and the previous finding that 751 cells do not express CD34 so that SAM.1 is not directed to the CD34 marker itself, it is apparent that SAM.1 recognizes a population of cells that co-express both the CD34 marker and SCPF.

The population of cells that are both CD34⁺ and SCPF⁺ represents 1.65% of the total cell population examined (FIG. 10). The ability of SAM.1 to recognize cell populations in murine, bovine, and ovine bone marrow was also examined by flow cytometry. In all cases, SAM.1 failed to recognize any significant population of cells from the bone marrow of these non-human species.

Flow cytometry studies were conducted on purified CD34⁺ cells using the anti-SCPF antibody. The CD34⁺ population had been separated from normal human bone marrow using using immunomagnetic beads coupled to anti-CD34 monoclonal antibodies and stored in liquid nitrogen prior to their use in flow cytometry (Kessler et al., 1987, Blood 70:321). On both single and two-color analysis, SAM.1 recognizes the CD34-selected population (FIG. 11). Furthermore, there is no competition between SAM.1 and anti-CD34 (FIG. 12). In these experiments, the CD34⁺ cells were either incubated with SAM.1 alone or a mixture of SAM.1/anti-CD34. As can be observed in FIG. 12, anti-CD34 did not interfere with the ability of SAM.1 to bind to these cells. These experiments were repeated with the exception that the CD34⁺ cells were incubated with anti-CD34 alone or with a mixture of SAM.1/anti-CD34. As shown in FIG. 12A, SAM.1 did not interfere with the binding of anti-CD34 antibody. This again indicates that SAM.1 antibody recognizes a distinct cell surface antigen.

7.2.4. Long Term Culture of CD34⁺ Cells Using SCPF from 751 Cells

Long-term cultures of the CD34⁺ cells were initiated in the presence of exogenously added purified native SCPF. Control cultures without any exogenously added growth factors, as well as cultures with 100 U/ml of interleukin 3 (IL-3) and 100 U/ml of interleukin 6 (IL-6) were included. Purified CD34⁺ cells were seeded into wells of a 24-well plate at 200,000 cells/ml and appropriate growth factors added. The purified SCPF was added at varying concentrations (1 ug/ml to 10 ng/ml). Every three days the culture media were changed and exogenous growth factors added. All cultures were examined daily to assess the viability and condition of the cells.

The results from these studies are summarized in FIG. 13. The cultures that received the IL-3 or IL-6 expanded rapidly with few non-viable cells present. By day 7, the cultures needed to be passaged. The SCPF treated cultures, on the other hand, underwent a rapid decline in cell viability such that by day 7, only 10-15% of cells were viable. However, this residual population of CD34⁺ cells are now SCPF responsive and have been proliferating in culture for twelve weeks. The control cultures (without growth factors) were maintained for 3 weeks before they eventually died out. The cells receiving the IL-3 or IL-6 are of mixed morphology and contain both adherent and nonadherent cells. Cytocentrifuged preparations show the cultures to contain many mature granulocytic cells as well as mature blast-like cells. These IL-3 and IL-6 treated cells were maintained in continuous culture for up to 16 weeks. The SCPF-treated cells are more uniform in size, are all mononuclear and blast-like in appearance, and are nonadherent. From the dose response experiment, it appears that the optimal concentration of SCPF lies between 50 ng/ml and 10 ng/ml.

At 12 weeks post culture, the SCPF-treated CD34+ cells were examined by flow cytometry for the presence or absence of CD34, CD38, and DR/HLA Class II expression. The data shown in FIGS. 14 and 15 illustrate that the SCPF-expanded CD34+ cells consist of two morphological populations based upon size. FIG. 14 (gated area C) shows small cells with the phenotype of CD34+, CD38− and DR−. The large population (FIG. 15—gated area B) is CD34+, CD38$^{low}$ and DR$^{low}$. Therefore, it appears that SCPF can induce proliferation of CD34+ cells in in vitro culture while maintaining their CD34+ phenotype—ie. the CD34+ cells proliferate without differentiation. Replating efficiency of both the SCPF-expanded CD34+ cells and the IL-3-expanded CD34+ cells were tested at 8 weeks post culture (Table 3).

the SCPF-expanded cells. SCPF does not confer any malignant phenotype on the CD34+ cells since the CD34+ cells died within 4–5 days after the SCPF was withdrawn.

The studies conducted on the ability of this growth factor to interact with bone marrow stem cells as a primary signal, indicate that SCPF is capable of inducing both BFU and CFU-GM colonies (FIGS. 16 and 17). SCPF does not appear to be able to induce CFU-GEMM. This factor, however, is capable of enhancing the activity of a mixture of colony stimulating factors (GM-CSF, IL-3 and EPO), thereby significantly increasing the CSF activity for BFU (FIGS. 16A and C), CFU-GM (FIGS. 17A and C), and CFU-GEMM (FIGS. 18A and C) colonies.

7.2.5. Induction of CD34+ Cells Into the Cell Cycle by SCPF

The following experiment analyzed the ability of SCPF and IL-3 to induce purified CD34+ bone marrow cells to replicate. The results demonstrate that both SCPF and IL-3 when given alone were capable of stimulating the cells to enter the cell cycle. When the two cytokines were added in combination to cultured cells, there is an additive effect on increasing the percentage of cells in the G2 phase (Table 4).

TABLE 3

Replicating Efficiency of CD34+ Cells Responsive to Stem Cell Proliferation Factor and Human Recombinant IL-3

| Cells$^\Phi$ | Treatment | r-IL-3 | | | | r-GM-CSF | | | |
|---|---|---|---|---|---|---|---|---|---|
| | | 100§ | 50 | 25 | 5 | 100 | 50 | 25 | 5 |
| CD34+ Expanded (8 wks) | r-IL-3 | 12† | 7 | 1 | 0 | 9 | 6 | 3 | — |
| CD34+ Expanded (8 wks) | SCPF | 162 | 109 | 92 | 41 | 145 | 114 | 62 | 31 |
| CD34+ Expanded (8 wks) | IL-6 | 18 | 11 | 6 | — | 15 | 12 | 4 | — |

† Number of colonies scored.
$^\Phi$ 10$^3$ cells/well.
§ Units/ml.

The data again suggests that the cells proliferated in the presence of IL-3 are poor in replating (using recombinant IL-3 and GM-CSF). On the other hand, the SCPF-treated CD34+ cells had good replating efficiency in the presence of IL-3 and GM-CSF, again indicating the primitive nature of

TABLE 4

Induction of CD34+ Cells Into The Cell Cycle By SCPF As Measured Flow Cytometry And Propidium Iodine

| | CD34+ CELLS | | | | |
|---|---|---|---|---|---|
| TREATMENT | — | MEM ALONE | IL-3$ | SCPF§ | ILI-3 + SCPF |
| CELL CYCLE PHASE | | | | | |
| G1 | 92.1% | 93.6% | 68.9% | 81.2% | 61.2% |
| G2 | 1.7% | 1.0% | 4.0% | 3.6% | 9.4% |
| S | 5.6% | 5.4% | 27.1% | 15.1% | 29.8% |

$ 100 U/ml of rHu-IL-3.
§ 100 ng/ml of SCPF.

7.2.6. Antibody Inhibition Studies

The following studies examined the use of polyclonal antibodies specific for human GM-CSF, G-CSF, M-CSF, and IL-3 to neutralize the blast cell colony formation induced by SCPF in methylcellulose bone marrow colony assays (Table 5).

TABLE 5

Colony Forming Activity of SCPF Inhibiton by Specific Antibodies

| | | | SCPF/Blast Cell Colony Counts | | |
|---|---|---|---|---|---|
| Cells | Antibody | Treatment | 100 ng/ml | 50 ng/ml | 25 ng/ml |
| BM$^a$ | anti-GM CSF | + | 24 | 16 | 8 |
| N/A | | − | 23 | 14 | 9 |
| BM | anti-G CSF | + | 21 | 13 | 6 |
| N/A | | − | 19 | 14 | 4 |
| BM | anti-M CSF | + | 26 | 14 | 5 |
| N/A | | − | 19 | 16 | 7 |
| BM | anti-IL-3 | + | 19 | 11 | 5 |
| N/A | | − | 17 | 10 | 5 |
| BM | SAM.1 | + | 8 | 2 | 0 |
| N/A | | − | 26 | 15 | 8 |

IL-3 (20 ng/ml)   IL-3 (20 ng/ml) +   GM (20 ng/ml)   GM (20 ng/ml) +

TABLE 5-continued

Colony Forming Activity of SCPF Inhibiton by Specific Antibodies

| | | | ALONE | SCF (100 ng/ml) | ALONE | SCF (100 ng/ml) |
|---|---|---|---|---|---|---|
| BM | SAM.1 | + | 24[b] | 59 | 31 | 92 |
| N/A | | − | 22 | 63 | 33 | 86 |

Clonogenic assay using 1 × 10[4] cells.
Total colonies observed.

The data shows that none of these polyclonal antibodies was capable of neutralizing the induction of blast cell colonies by SCPF whereas SAM.1 was able to neutralize their induction. However, SAM.1 antibody was unable to inhibit human stem cell factor (SCF) enhancement of GM-CSF and IL-3. This indicates that SCPF is not identical to the known CSF's and since SAM.1 antibody does not inhibit the function of SCF, SCPF appears to be functionally different to SCF.

7.2.7 Two-Dimensional Gel Electrophoresis

Chemicals. Acrylamide, N,N'-methylenebisacrylamide, urea, ammonium persulfate, N,N,N,N-tetramethylethylenediamine and AG 501-X8 analytical grade mixed bed resin were purchased from Bio-Rad (Rockville Centre, N.Y.). Pharmalyte pH 3–10 and Biolyte pH 3–10 ampholytes and molecular weight standards ($M_r$ 20,100, trypsin inhibitor, soybean; 24,000, trypsinogen; 29,000, carbonic anhydrase; 36,000, glyceraldehyde-3-phosphate dehydrogenase; 45,000, albumin, egg; 66,000, albumin, bovine; 97,400, phosphorylase B; 116,000, β-galactosidase), were from the Sigma Chemical Co. (St. Louis, Mo.). The BCA Protein Assay Reagents were from Pierce (Rockford, Ill.). All other chemicals were analytical grade and were from either Fisher Scientific or the Sigma Chemical Co.

First Dimension. Isoelectric focusing gels (IEF) (O'Farrell, *J. Biol. Chem.*, 250:4009, 1975) were made in 11 cm glass tubes with an inner diameter of 0.3 cm, which were sealed at the bottom with Parafilm. The tube gels, which contained 4% acrylamide, 9M urea, 2% Nonidet P-40 and 2% ampholytes, were prepared in two steps. First, the following components were mixed and gently agitated in the presence of AG 501-X8 resin (45 mg/ml mixture) for approximately 10 minutes: 2.5 ml acrylamide stock solution (38% (w/v) acrylamide and 2% (w/v) N,N'-methylenebisacrylamide in $H_2O$), 5.0 ml 10% (w/v) Nonidet P-40 in $H_2O$, 13.75 g urea and 3.75 ml $H_2O$. The acrylamide mixture was then filtered through a glass wool plug to remove the resin. Second, for each protein, gels were prepared by mixing 4.23 ml acrylamide mixture, 5% pH 3–10 ampholytes (50% Pharmalytes and 50% Biolytes), an appropriate volume of solubilized protein sample and deionized water to give a total volume of 4.98 ml. After degassing for approximately 2 minutes, 5.0 µl freshly prepared 10% (w/v) ammonium persulfate and 3.5 µl N,N,N,N-tetramethylethylenediamine were added. Gels were quickly cast (0.76 ml gel mixture/tube), overlayed with deionized water and allowed to polymerize for 3 hours. All protein samples were centrifuged for 3 minutes at 13,000×g prior to being added to the gel mixtures.

The tubes were placed in a Bio-Rad Model 155 gel electrophoresis cell containing 0.01M phosphoric acid in the lower (anode) chamber and degassed 0.02M sodium hydroxide in the upper (cathode) chamber. Electrofocusing was carried out at room temperature for 18 hours using a constant voltage of 350 V. When electrofocusing was completed, the gels were gently extruded from the glass tubes by attaching an air-filled syringe/rubber tubing assembly to the basic ends of the tubes and applying a small amount of pressure. The IEF pH gradient was determined using a surface electrode (Bio-Rad). Gels were then gently agitated in 5.0 ml equilibration buffer (2.3% sodium dodecylsulfate, 5% β-mercaptoethanol and 10% (v/v) glycerol in 0.062M Tris-HCl, pH 6.8) for 10 minutes or were quickly frozen in an ethanol/dry ice bath and stored at −70° C. until use.

Second Dimension. Samples were separated by slab SDS-PAGE on 10% gels (1.5 mm thickness, 14.5 cm length) with a 4% acrylamide stacking gel according to the method of Laemmli. The first-dimension IEF gels and molecular weight standards, which were embedded in 1% agarose in equilibration buffer, were attached to the stacking gel using 1% agarose in 0.125M Tris-HCl, pH 6.8. Electrophoresis was carried out at room temperature (20°–25° C.) using a constant current of 100 mA/gel until the dye had run to about 100% of the length of the gel.

Fixation and Staining. The separated proteins within the second-dimension slab gels were fixed overnight in methanol/acetic acid/water (40/10/50). Fixed gels were stained with Coomassie blue by standard techniques or silver stained according to the following modifications. Fixed gels were washed for a minimum of 1 hour in 3 changes of 20% ethanol prior to staining. Staining was done by standard methods (Merril, et al., *Methods Enzymol.*, 104:441, 1984). Gels were allowed to stain for 30–45 minutes with constant gentle agitation. The stained gels were then washed for a total of 20 minutes in two changes of 20% ethanol prior to developing the stain. Stain development was stopped by placing the gels in ethanol/acetic acid/water (20/10/70). Background staining was removed by placing the gels in Kodak Rapid Fixer (film strength) for 2–5 minutes. Gels were then washed for a total of 30 minutes in 3 changes of water followed by 5 minutes in Kodak hypo clearing agent to remove the fixative from the gel. The hypo clearing agent was removed from the gels by washing for a minimum of 1 hour in 3 changes of 20% ethanol. Finally, the stained gels were dried at room temperature by wrapping each gel between two sheets of BioGelWrap (BioDesign, Inc., Carmel, N.Y.).

Photography of stained gels. Direct prints of the silver-stained gels were made with Kodak Electrophoresis Duplicating Film according to the manufacturer's instructions. This film produces a permanent record of the proteins found in a gel and permits visual matching of protein patterns across several gels with the aid of a light box. In a few cases, gels were photographed using Kodak Ektapan 4×5 inch sheet film and printed onto 16×20 inch Orthofilm. The resulting prints showed the protein spots as large black dots on a clear film base. The large format of these prints was easy to examine and allowed accurate records of protein pattern differences to be noted directly on the print.

7.2.8 Bioassay for SCPF Activity

The presence or absence of SCPF in protein(s) eluted from SDS-page gels, either 1-D or 2-D, was measured in a proliferation assay using [$^3$H]-methyl thymidine ([$^3$H]Tdr)

incorporation by a CD34+ cell line (ML-1) developed in our laboratory (see Section 8.1). Alternatively, other CD34+ cells, such as KG-1a CD34+ cells (ATCC CCL 246.1), can be used in the assay to test preparations for SCPF activity.

Briefly, $1 \times 10^5$ ML-1 cells were seeded into wells of a round bottom 96-well microtiter plate in a volume of 100 µl/well of Iscoves modified Dulbecco's medium containing 10% FBS and L-glutamine. Serial two-fold dilutions of putative SCPF protein preparations were added (100 µl/well) to triplicate wells. The cultures were then incubated for 48 hours at 37° C. in a humid atmosphere of 5% $CO_2$ in air. Following incubation, the cultures were labelled with 1 µCi of [$^3$H]-Tdr/well for the last 16–18 hours of culture. The amount of radioisotope incorporation was quantitated by liquid scintillation counting. Tables 6 and 7 show tritiated thymidine incorporation for bioassays using KG-1a and ML-1 cells, respectively. Two-fold dilutions of putative SCPF isolated from the 37 kD protein from an SDS-PAGE (see section 7.1.2.) were tested and the results of tritiated thymidine incorporation showed that SCPF bioactivity was present in the preparation (compared with the control).

Using a preparation isolated from the 37 kD protein identified on SDS-PAGE, a 2-D gel was run. After staining with Coomassie blue, multiple isoforms of SCPF were identified on the 2-D gel. The gel was divided into sections and 8 slices containing protein were removed. Proteins were eluted from the 8 slices as described in 7.1.2. above. Bioassays were performed on the eluted proteins from each slice. Incorporation of tritiated thymidine correlated with protein preparations made from the isoforms found in slice #4 (Table 8, data is shown in CPM). SCPF isoforms identified in slice #4 represent proteins in the pH 7.0 to 8.0 range, as determined by surface electrode analysis. The bioactivity in this fraction demonstrated the classic dilution effect as seen by two-fold dilution of cytokines in bioassay.

The bioactivity data identified in Table 8 was further verified by western blot analysis using the SAM.1 antibody. Two-dimensional gels run as described above (pH gradient gels and subsequent molecular weight gels) were blotted onto nitrocellulose or PVDF filters and hybridized using standard hybridization techniques using SAM.1 as a primary antibody and Alkaline Phosphatase-conjugated Goat anti-Rabbit IgG (H & L) as the secondary antibody (BioRad). The data revealed that the antibody strongly reacts with protein in the pH range of 7.0–8.0, consistent with the region which exhibited SCPF bioactivity.

SCPF can be further purified to homogeneity from discrete spots on a 2-D gel by standard immunoaffinity techniques using SAM.1 or other SCPF-specific antibodies (Current Protocols in Immunology, Chapter 8, Coligen, et al., eds., 1992). SCPF is eluted from the immunoaffinity matrix and then subject to isoelectricfocusing, as described above, but in a narrower pH range of pH 6–8, preferably. The protein separated in the gel can then be screened for SCPF bioactivity in the bioassay described above.

TABLE 6

SCPF BIOASSAY
KG-1a CELLS
µg/ml SCPF (37 kDa prep) - Mean of Three Samples

|         | 1       | 0.5     | 0.250   | 0.125   | 0.063   |
|---------|---------|---------|---------|---------|---------|
| CPM     | 120,196 | 118,351 | 73,472  | 41,700  | 39,748  |
| S.D. (+/−) | 36,890  | 13,105  | 13,060  | 7,733   | 1,281   |
|         | 0.031   | 0.016   | 0.008   | 0.004   | 0.002   | Control |
| CPM     | 39,052  | 40,874  | 40,586  | 40,530  | 41,852  | 44,884 |
| S.D. (+/−) | 5,019   | 3,308   | 3,350   | 3,175   | 2,392   | 7,499  |

TABLE 7

SCPF BIOASSY
ML-1 CELLS
µg/ml SCPF (37 kDa prep) - Mean of Three Samples

|         | 1       | 0.5     | 0.250   | 0.125   | 0.063   |
|---------|---------|---------|---------|---------|---------|
| CPM     | 115,151 | 99,383  | 90.586  | 89,309  | 49,462  |
| S.D. (+/−) | 7,737   | 7,332   | 2,702   | 4,593   | 1,659   |
|         | 0.031   | 0.016   | 0.008   | 0.004   | 0.002   | Control |
| CPM     | 54,680  | 53,180  | 50,606  | 54,161  | 53,432  | 48,020 |
| S.D. (+/−) | 5,099   | 4,107   | 1,101   | 1,799   | 1,076   | 4,120  |

TABLE 8

GEL FRACTIONS (1–8) - SCPF BIOASSAY ML-1 CELL LINE
Dilutions of Recovered Protein - Mean of Three Samples

| CPM         | 1:3   | 1:6  | 1:12 | 1:24 | 1:48 | 1:96 | 1:192 | Control[a] |
|-------------|-------|------|------|------|------|------|-------|---------|
| Slice #1-CPM | 4115  | 1501 | 6177 | 4891 | 5934 | 4191 | 4377  | 0       |
| Slice #2-CPM | 6853  | 3568 | 5837 | 5216 | 5306 | 5976 | 5493  |         |
| Slice #3-CPM | 229   | 4358 | 3427 | 4310 | 3625 | 5012 | 1313  |         |
| Slice #4-CPM | 13454 | 9386 | 8631 | 8214 | 8722 | 1600 | 0     |         |
| Slice #5-CPM | 0     | 884  | 6936 | 0    | 0    | 0    | 2353  |         |
| Slice #6-CPM | 1302  | 0    | 3251 | 1817 | 948  | 636  | 0     |         |
| Slice #7-CPM | 0     | 0    | 0    | 0    | 2606 | 4480 | 3687  |         |
| Slice #8-CPM | 5209  | 0    | 0    | 1209 | 0    | 4650 | 2162  |         |

[a]control mean CPM = 48,020 ± 4,120 S.D.

7.2.9 Sequence Analysis of SCPF from Murine 751 Cell Line

The 17 kDa fragment of the 37 kDa protein was concentrated and purified from conditioned serum-free supernatents of 751 cells grown in RPMI-1640 media. Briefly, 751 cells were propagated in RPMI-1640 media containing 10% FCS until about 80% confluent. The cultures were then washed 2× with PBS and cultured in serum free RPMI. Twelve hours after incubation, cells were harvested and supernatant collected and clarified by low speed centrifugation at 4° C. The supernatant was lyophilized to dryness and stored at −20° C. The lyophilized protein was resuspended in 0.1% trifluoroacetic acid (pH 1.9) and dialyzed overnight at 4° C. followed by low speed centrifugation.

About 200 μl of the preparation was injected into a reverse phase HPLC column (Waters, Novapak-C18) equilibrated in 0.1% TFA, pH 1.9 and eluted with a linear gradient of 0–20% acetonitrile in 0.1% TFA, pH 1.9 for 10 minutes followed by elution with 20%–60% acetonitrile in 0.1% TFA, pH 1.9 for one hour. Fractions were collected and aliquots of each analyzed using Western analysis with SAM.1 antibody. SAM.1 positive polypeptide eluted in the range of 30–33% acetonitrile. The sample was then purified by SDS-PAGE.

The SAM.1 positive polypeptide migrated at about 17 kD. This band was cut out of the SDS gel and digested with Lysyl-C endopeptidase to form fragments. The fragments were fractionated on a reverse phase C8 column (Waters). Peptides were then sequenced using an automated amino acid sequencer as described (Hunkapeller, et al., In: Methods of Protein Microcharacterization, Gas-phase protein/peptide sequencer., D. E. Shireley, ed., Clifton, N.J., Humana Press, pp. 223–247, 1986).

Four peptides which were unique according to a protein database (Dayhoff) search were synthesized for production of antipeptide antisera. Antibodies were raised (in rabbits by HTI Bio-Products, Ramona, Calif.) against the peptides as follows. The initial immunization at Day 0 was 300 μg antigen emulsified in complete Freund's adjuvant (CFA). Boosts at 21, 42, and 63 days were 300 μg antigen emulsified in incomplete Freund's adjuvant (IFA). The rabbits were bled at each of the inoculation time points and at 49, 77, and 84 days post-inoculation and the serum tested with 751 cell lysates by Western Blot for the presence of antibody reactive to SCPF proteins.

Antibody which was synthesized against the peptide, Lys, Asp, Arg Gly Pro Ala Gly Ala Leu (SEQ ID NO: 1), reacted specifically with two proteins (17 kDa and 37 kDa) on a Western blot. FIG. 19 shows a Western blot analysis of anti-peptide sera reactivity with: Lanes 1, 2, and 3: 751 cell lysate (RPMI+10% FBS), 15 μl, 30 μl, and 40 μl, respectively; Lanes 4, 5, and 6: 751 cell lysate (RPMI+10% FBS)+50% serum-free supernatant from ML-1 cells; 15 μl, 30 μl, and 40 μl, respectively; Lanes 7, 8, and 9 show 30 μl of 751 NA cell lysate blotted with preimmune sera as a negative control.

The 37 kDa band was cut from the gel and extracted as described above and tested for bioactivity by colony assay of hematopoietic cells as described in 8.4 below.

7.2.10 Assay for Synergy with Other Growth Factors

ML-1 cell line was isolated and purified from CD34$^+$ cells which were immunoselected from bone marrow from human cadaveric vertebral bodies (see Section 8.1). Immunoselected CD34$^+$ cells were stained with CD34-PE, CD38-FITC and Cr-PerCP prior to and subsequent to exposure to cytokines. CD34$^+$ cells (2×10$^5$) were cultured in 1.0 ml Dulbecco's medium plus or minus various cytokines alone or in combination (see Tables 9 and 10). Cells were counted prior to culture and again after 6 days of culture. Cells were then stained with the SCPF antibody, SAM.1, and subjected to FACS analysis. CD34$^+$ cells were gated in list mode according to side scatter and PE fluorescence. Two distinct size populations of the CD34$^+$ cells, large and small, were identified based upon forward light scatter. These cells were analyzed for CD38 and Dr expression. The data is given for the large and small CD34$^+$ cell population in Tables 9 and 10, respectively. These results show that SCPF and IL-3, when given alone, were capable of stimulating cells to enter the cell cycle. The combination of SCPF+IL-3 has an additive and possibly synergistic effect in increasing the total number of large CD34$^+$ cells, as well as small CD34$^+$ cells.

TABLE 9

CD34$^+$ LARGE CELLS

| Cytokines | Large CD34$^+$ Cells/30,000 | Total No. Cells/Well | Total Large CD34$^+$ Cells | 38$^-$ Dr$^+$ (%) Total | 38$^+$ Dr$^+$ (%) Total | 38$^-$ Dr$^-$ (%) Total | 38$^+$ Dr$^-$ (%) Total |
|---|---|---|---|---|---|---|---|
| Pre-culture | 8,662 | 2.0 × 10$^5$ | 57,480 | 841 (9.8) 5,663 | 1,651 (19.1) 10,979 | 3,352 (38.9) 22,360 | 2,778 (32.2) 18,508 |
| Media | 5,814 | 6.5 × 10$^4$ | 12,597 | 521 (9.0) 1,134 | 3,076 (52.9) 6,664 | 1,164 (20.0) 2,519 | 1,053 (18.1) 2,280 |
| IL-6 | 8,132 | 1.5 × 10$^5$ | 40,660 | 1,455 (17.9) 7,278 | 4,177 (51.4) 20,899 | 1,602 (19.7) 8,010 | 898 (11.0) 4,472 |
| SCF | 10,623 | 2.6 × 10$^5$ | 92,066 | 478 (4.5) 4,143 | 4,640 (43.7) 40,233 | 1,285 (12.1) 11,140 | 4,220 (39.7) 36,550 |
| SCPF | 8,575 | 1.6 × 10$^5$ | 45,733 | 1,634 (19.1) 8,739 | 4,270 (49.8) 22,775 | 1,397 (16.3) 7,454 | 1,274 (14.9) 6,814 |
| IL-3 | 8,747 | 5.3 × 10$^5$ | 154,530 | 504 (5.8) 8,963 | 4,844 (55.4) 85,610 | 719 (8.2) 12,671 | 2,680 (30.6) 47,286 |
| IL-3 + IL-6 | 8,927 | 4.3 × 10$^5$ | 127,954 | 579 (6.5) 8,317 | 5,143 (57.6) 73,701 | 742 (8.3) 10,620 | 2,463 (27.6) 35,315 |
| IL-3 + SCF | 9,482 | 9.8 × 10$^5$ | 309,745 | 194 (2.0) 6,195 | 3,643 (38.4) 118,942 | 1,723 (18.2) 56,374 | 3,922 (41.4) 128,234 |
| IL-3 + SCPF | 8,230 | 8.3 × 10$^5$ | 227,697 | 529 (6.4) 14,573 | 4,510 (54.8) 124,778 | 679 (8.3) 18,899 | 2,512 (30.5) 69,448 |

TABLE 9-continued

CD34+ LARGE CELLS

| Cytokines | Large CD34+ Cells/30,000 | Total No. Cells/Well | Total Large CD34+ Cells | 38− Dr+ (%) Total | 38+ Dr+ (%) Total | 38− Dr− (%) Total | 38+ Dr− (%) Total |
|---|---|---|---|---|---|---|---|
| IL-6 + SCF | 11,684 | 5.6 × 10⁵ | 218,101 | 105 (0.9) 1,963 | 4,481 (38.4) 83,751 | 1,471 (12.6) 27,481 | 5,627 (48.2) 105,125 |
| IL-3 + IL-6 + SCF | 8,721 | 1.5 × 10⁶ | 436,050 | 106 (1.2) 5,233 | 3,228 (37.0) 161,338 | 1,479 (17.0) 74,128 | 3,908 (44.8) 195,350 |
| IL-3 + IL-6 + SCPF | 8,683 | 8.0 × 10⁵ | 231,547 | 484 (5.6) 12,967 | 4,900 (56.4) 130,592 | 705 (8.1) 18,755 | 2,594 (29.9) 69,232 |
| IL-3 + IL-6 + SCR + SCPF | 8,431 | 1.9 × 10⁶ | 533,963 | 143 (1.7) 9,077 | 3,226 (38.3) 204,508 | 1,172 (13.9) 74,221 | 3,890 (46.1) 246,157 |

100 μ/ml rHu-IL-3; 100 ng/ml SCPF; 100 ng/ml SCF; 100 μ/ml rHu-IL-6

TABLE 10

CD34+ SMALL CELLS

| Cytokines | Small CD34+ Cells/30,000 | Total No. Cells/Well | Total Small CD34+ Cells | 38− Dr+ (%) Total | 38+ Dr+ (%) Total | 38− Dr− (%) Total | 38+ Dr− (%) Total |
|---|---|---|---|---|---|---|---|
| Pre-culture | 15,149 | 2.0 × 10⁵ | 100,993 | 1,585 (10.5) 10,604 | 2,819 (18.6) 18,785 | 6,512 (43.0) 43,426 | 4,233 (27.9) 28,177 |
| Media | 6,090 | 6.5 × 10⁴ | 13,195 | 1,308 (21.5) 2,837 | 2,141 (35.2) 4,645 | 2,063 (33.9) 4,473 | 578 (9.5) 1,254 |
| IL-6 | 2,638 | 1.5 × 10⁵ | 1,3190 | 571 (21.6) 2,849 | 698 (26.5) 3,495 | 1,037 (39.3) 5,184 | 332 (12.6) 1,662 |
| SCF | 1,227 | 2.6 × 10⁵ | 10,634 | 116 (9.5) 1,010 | 333 (27.1) 2,882 | 455 (37.1) 3,945 | 323 (26.3) 2,797 |
| SCPF | 1,616 | 1.6 × 10⁵ | 8,619 | 381 (23.6) 2,034 | 307 (19.0) 1,638 | 757 (46.8) 4,034 | 171 (10.6) 913 |
| IL-3 | 945 | 5.3 × 10⁵ | 16,695 | 136 (14.4) 2,404 | 147 (15.6) 2,604 | 407 (43.1) 71,96 | 255 (27.0) 4,508 |
| IL-3 + IL-6 | 761 | 4.3 × 10⁵ | 10,908 | 85 (11.2) 1,222 | 146 (19.2) 2,094 | 377 (49.5) 5,399 | 153 (20.1) 2,192 |
| IL-3 + SCF | 1,197 | 9.8 × 10⁵ | 39,102 | 19 (1.6) 626 | 228 (19.0) 7,429 | 360 (30.1) 11,770 | 590 (49.3) 19,277 |
| IL-3 + SCPF | 1,088 | 8.3 × 10⁵ | 30,101 | 94 (8.6) 2,589 | 256 (23.5) 7.074 | 404 (37.1) 11,167 | 334 (30.7) 9,241 |
| IL-6 + SCF | 1,335 | 5.6 × 10⁵ | 24,920 | 31 (2.3) 573 | 258 (19.3) 4,809 | 450 (33.7) 8,398 | 596 (44.6) 11,114 |
| IL-3 + IL-6 + SCF | 1,555 | 1.5 × 10⁶ | 77,750 | 20 (1.3) 1,011 | 320 (20.6) 16,016 | 373 (24.0) 18,660 | 842 (54.1) 42,063 |
| IL-3 + IL-6 + SCPF | 1,022 | 8.0 × 10⁵ | 27,253 | 94 (9.2) 2,507 | 177 (17.3) 4,715 | 463 (45.3) 12,346 | 288 (28.2) 7,685 |
| IL-3 + IL-6 + SCR + SCPF | 687 | 1.9 × 10⁶ | 43,510 | 22 (3.2) 1,392 | 1990 (27.7) 12.052 | 283 (41.2) 17,296 | 192 (27.9) 12,139 |

100 μ/ml rHu-IL-3; 100 ng/ml SCPF; 100 ng/ml SCF; 100 μ/ml rHu-IL-6

8. EXAMPLE: STEM CELL PROLIFERATION FACTOR DERIVED FROM HUMAN ML-1 CELL LINE

The experiments described below indicate that SCPF from human cell line ML-1 has a molecular weight of about 23 kDa and a pI of about 7.7 as determined by 2D gel electrophoresis in the presence of urea and about 27 kDa as determined from one dimensional gel electrophoresis.

8.1 Origin of ML-1 Cell Lines

A heterogeneous population of CD34+ enriched bone marrow cells was prepared from human cadaveric vertebral bodies (see, generally, La Russa, et al., Exp. Hem., 20:442, 1992; Stanley, et al., J. Immunol., 149:689, 1992; Kessler, et al., Blood (Suppl. 1), 70:321a, 1987). These cells were in vitro cultured ($10^5$ cells/well in 48 well plate) in Iscoves modified Dubbeccos Minimal Essential Medium (IMDM) supplemented with 20% fetal bovine serum (FBS), L-glutamine, penicillin/streptomycin and 100 ng/ml SCPF from cell line 751 at 37° C. in an atmosphere of 5% $CO_2$ in air.

Every 3 days the exogenous SCPF from cell line 751 was replenished (100 ng/ml) for a period of 42 days. During this time cell counts were done on a daily basis. Viable cell numbers decreased around day 9–10 of culture. At approximately day 14 of culture the cells appeared to become responsive to SCPF from cell line 751 as evidenced by cell proliferation.

After 42 days of initial culture the remaining cells were subcultured and maintained in the above culture media which was supplemented with SCPF (100 ng/ml) from cell line 751 once a week. Approximately 4–6 weeks into sub-culture it was evident that the cells could now grow in the absence of exogenous SCPF from cell line 751. This suggested that the cell line (ML-1) might be capable of producing its own proliferative factor. The ML-1 cell line was then analyzed to define the repertoire of inherent cell surface markers present and found to be $CD34^+$, $HLA^-$, $DR^+$, $CD38^-$, $CD2^-$, $CD3^-$, $CD4^-$ and $CD8^-$. Table 11 shows the results of the flow cytometry phenotype analysis.

TABLE 11

FLOW CYTOMETRY PHENOTYPE OF ML-1 CELLS

| MARKER | FLUORESCENT CELLS[1] |
|---|---|
| CD2 | 0 |
| CD3 | 1.09 |
| CD19 | 0.79 |
| CD33 | 24.69 |
| CD38 | 2.39 |
| CD5 | 0 |
| CD8 | 0 |
| CD34 | 66.01 |
| CD4 | 11.88 |
| HLA-DR | 68.51 |
| HLA-1 (A, B, C) | 15.75 |
| CD56 | 0 |
| CD11a | 82.43 |
| CD18 | 46.86 |

[1]Mean percentage (n = 3) of positively fluorescent cells

In addition, ML-1 cells were subjected to karyotype analysis and various inversions and translocations were found. The specific pattern is as follows: 46, XY, del (4 q), −5, del (7 q), −8, +i (8 q) x2, −12, +der (12) t (8 q; 12 q), del (16 q), −17, +der (17)t (5 q; 17 q), 20p+.

8.2 Gel Purification of SCPF

ML-1 cells were grown to late log phase and solubilized with 0.1% Triton X-100 in TBS containing 2 µg/ml aprotinin. Cell lysates were electrophoresed on 1D Tris-tricine gels (Schagger and von Jagow, Anal. Biochem., 166:368, 1987) to get an estimate of the mass and on isoelectric focusing gels (pI 3–10, FMC) to get an estimate of the isoelectric point.

One-dimensional gel electrophoresis of the total cell lysate in sodium dodecyl sulfate (SDS) was performed using Tris-tricine gels (Schagger and von Jagow, Anal. Biochem., 166:368, 1987). The concentration of acrylamide was 5% T, 3% C for the stacking gel and 10% T, 3% C for the separator gel. Gels were stained either with Coomassie blue or blotted onto Immobilon-P (PVDF) membranes and probed with anti-SCPF antibody (SAM.1) by Western techniques. Western blotting was done by standard methods. The PVDF membranes were blocked with 5% blotto (Carnation non-fat dry powder milk) made in Tris-saline, pH 8, containing 0.05% Tween-20. Primary antibody, (SAM.1) was diluted 1 to 1,000 in blotto and was allowed to incubate with the blot for 2 hours at room temperature or overnight in the cold. Second antibody was alkaline-phosphate linked anti-rabbit antibody which was diluted 1 to 5,000 in blotto and incubated with the blot in the same manner as described above. Immunoreactive proteins were disclosed by incubating the blots with a substrate for alkaline phosphatase by standard procedures. On fresh preparations, the antibody disclosed a single band of about 27 kDa. Preparations that were stored for short periods at 4° C., on the otherhand, gave rise to two bands, a major one of about 27 kDa and a second, less intense band, around 14.5 kDa. The intensity of the 14.5 kDa band increased upon longer storage, suggesting that this band was derived from the 27 kDa band by some proteolytic event.

To determine the pI of human SCPF, the triton lysate was first passed through Amicon microconcentrators to concentrate the fraction and to exchange out the salt for 10 mM Tris buffer, pH 7, containing 0.06% CHAPS. Proteins were focused using IsoGel Agarose IEF (FMC) gels (pI range 3 to 10) using flatbed electrophoresis (BioRad). After focusing, proteins were transferred to Immobilon P membranes by press-blotting for 30 minutes in Tris-saline buffer, pH 7.5. SCPF was identified by Western blot using anti-SCPF antibody (SAM.1) and alkaline phosphatase linked second antibody. Using this method two bands were identified at pI 5.15 (14.5 kDa) and pI 9 (27 kDa).

For 2D gel electrophoresis proteins from cell lysates solubilized in 0.1% Triton X-100, as described above, were separated by 2D gel electrophoresis according to the procedure of Semple-Rowland, et al., Electrophoresis, 12:307, 1991. The first dimension was a 5% acrylamide isoelectric focusing gel in 7M urea extending between pH 5 and 9. Carrier ampholytes (Pharmacia) were used at concentrations of 4% v/v pH range 3–10. 300 ug total protein was added to the first dimension gel mixture before polymerization. Samples were electrophoresed at 750 v for 16 hours at room temperature and finally at 1000 v for 1 hour. The pH was measured using a surface electrode. The second dimension, a 12% acrylamide SDS slab gel, 1 mM thick, was electrophoresed at constant current (20 mA/gel) until the bromophenol blue dye marker reached the bottom of the gel. Gels were either stained with Coomassie blue or silver (Wray, et al., Anal. Biochem., 118:197, 1981) or electroblotted to Immobilon P (PVDF) membranes (Millipore). Molecular weight standards (200, 97, 69, 46, 30 and 21.5 kDa, Amersham Rainbow markers) were used to calibrate the gels in the second dimension.

The 2D gel and blot indicated that only two spots in the whole cell lysate interact with the antibody. This gel was run in 8M urea which removes protein structure, thus some amino acids that were buried in the intact molecule were exposed. Consequently, the small band had an apparent mass of 17 kDa and a pI of about 7.05. The large band had an apparent mass of 23 kDa and a pI of about 7.7. The difference in the values obtained in the flatbed IEF gel and the 2D gel is probably due to the presence of urea. In the flatbed IEF system, no urea was used and, consequently, the proteins should not have been unfolded.

Examination of a second blot of the same gel stained with Aurodye and the silver stained gel after blotting, revealed a well resolved intense spot with a mass of 23 kDa and a less intense spot of 17 kDa corresponding to the positions disclosed by the antibody. These spots were also seen in a companion gel stained with Coomassie blue.

8.3 Ion Exchange Purification of SCPF

SCPF was purified from ML-1 lysates by chromatography on DEAE-cellulose (DE52, Whatman), and CM-cellulose (BioRad, prepacked column). The 14.5 kDa protein (pI 5.15) adsorbed to DEAE in 10 mM Tris-HCl, pH 7, 0.06% CHAPS, and 1 mM PMSF. The column was developed with a linear 0 to 1.0M NaCl gradient. The 14.5 kDa protein eluted between 0.2M and 0.35M NaCl. The 27 kDa protein (pI 9) did not bind to DEAE, however, a large proportion of cellular proteins do bind and are therefore removed by this step. The flow through fraction was collected and dialyzed against 10 mM MES, pH 6.0 and analyzed by chromatography on CM-cellulose equilibrated in the same buffer. The CM-cellulose column was also developed with a linear NaCl gradient as described above. Again, the 27 kDa protein does not bind appreciably to this column under these conditions, but is separated from a second set of cellular proteins that do bind.

The sample was recovered by chromatography through a Mono S column which binds the protein. This column is developed with a linear gradient of NaCl (from 0.1 to 0.5M) is 50 minutes. Two protein peaks crossreacted well with the anti-SAM antibody. The first peak eluted with 50 mM NaCl, and the second with 100 mM NaCl. The second peak gave a stronger reaction with the antibody on Western blots. The two fractions contained several of the same proteins as determined by 2-D gel electrophoresis and western blot analysis with the anti-SAM antibody.

8.4 Bioactivity of Human SCPF from ML-1

Fractions from the flatbed immuno electrophoretic gel described above were tested using a commercial bioassay method (Almar Biosciences Inc., Sacramento, Calif.). This assay incorporates a fluorometric/colormetric growth indicator based on detection of metabolic activity. This redox indicator fluoresces and changes color as the cell growth media is reduced by cell proliferation.

KG-1A cells (ATCC CCL 246-1) were seeded at $1 \times 10^5$ cells/well of a 96-well microplate in volumes of 100 µl. To duplicate wells was added (100 µl) dilutions of samples to be tested for bioactivity as shown by an increase in rate of proliferation. Plates were then incubated for 48 hours at 37 C.° in an humidified atmosphere of 5% $CO_2$ in air. Following incubation, Alamar blue reagent was added in an amount equal to 10% of the culture volume (20 µl) and the plates returned to the incubator for an additional 6 hours. Color change was measured at a wavelength of 570 nm. The background absorbance was measured at 600 nm and subtracted out. The data illustrated in FIGS. 20A and B are the absorbance minus background. The samples tested were regions from pH 9.0 (A) and 5.0 (B) of an IEF gel in which the lysate from ML-1 cells had been focused. These regions (I-9.1–I-9.4 and I-5.1–I-5.6) were also analyzed for immunoreactivity (Western blot analysis) with SAM.1 antibody. Bioreactivity was observed in the pI-9.0 regions only. Sample I-9.3 appeared to have the greatest bioreactivity. No activity was observed in any of the pI 5.0 fractions tested. Using this bioassay technique, the protein isolated and purified (pI 7.7, 23 kDa) from the 2-D gel described above is found to be a human SCPF peptide.

In addition, the partially purified preparation recovered after chromatography was tested in clonogenic assays as previously described (see, *Colony Assays of Hematopoietic Cells Using Methylcellulose Media. An Introductory Technical Manual.* Prepared by the staff of the Terry Fox Laboratory Media Preparation Service, Vancouver, B.C., Canada V5Z 1L3, 1992) for stimulation of cell proliferation in immuno-selected human bone marrow CD34+ cells. Briefly, diluted cells were added to pre-aliquoted tubes of Ready-Mix Methylcellulose at 10 times the final concentration required in the dish (e.g., by adding 0.3 ml of $2 \times 10^6$ cells per ml to a 15 ml tube containing 3 ml of Ready-Mix where duplicate assay cultures are desired, or by adding 0.5 ml to a 15 ml tube containing 5 ml of Ready-Mix where quadruplicate assays are desired). This gives a final concentration of $2 \times 10^5$ cells per 1.1 ml of final plating mixture. A ten-fold concentration of cell suspension allows the cells to be added as one tenth of the final volume. If the Ready-Mix Methylcellulose has been purchased as a large volume (e.g., 100 ml per bottle), this entire volume should have been aliquotted beforehand as 3 ml of 5 ml volumes into the 15 ml tubes using a 5 ml disposable syringe and a 16 gauge blunt end needle. Immediately after adding the cells to the tube, the contents were vortexed vigorously until the cells were evenly suspended (3 ml of the final methylcellulose mixture will rise approximately two-thirds of the way up the sides of the tube.) After vortexing, the tube was left for a few minutes to let any large air bubbles present rise to the surface (5 minutes is sufficient). (Note that since this is the mixture in which the cells are cultured, the cells can be left in this state for a few hours at room temperature before plating, if necessary, without adversely affecting subsequent colony formation). Next, the final cell-containing mixture was plated in 1.1 ml volumes into sterile 35 mm petri dishes. For each tube plated, a new sterile disposable 3 ml syringe fitted with a 16 gauge blunt end needle was used. The dishes were then placed in pairs inside 100 mm petri dishes. A third 35 mm dish (without its lid) was added for a water dish. The purpose of the water dish is to ensure that maximum humidity is attained during the subsequent 2–3 week incubation period. The 35 mm petri dishes used for the assay cultures were pre-tested for their inability to allow fibroblast attachment and growth. This occurs readily when marrow cells are cultured in the so-called petri (non-tissue culture) dishes sold by most suppliers, and when this happens hematopoietic colony formation is often obscured or even inhibited. The viscous methylcellulose mixture was spread evenly across the surface of each dish by rotating and tilting the dish to allow the meniscus to attach to the wall of the dish on all sides. 3 ml of sterile water was added to each water dish.

The cultures were placed on a level tray in a 37° C. humidified incubator and maintained at an internal atmosphere of 5% $CO_2$ in air. After 10 to 12 days of incubation, the culture dishes were removed and, one at a time, placed (with the lid still on) inside a 60 mm gridded tissue culture dish to score the colonies in situ using an inverted microscope. Counts included the smaller erythroid colonies derived from the most mature types of erythroid colony-forming cells (i.e., from CFU-E and mature BFU-E). The dishes were then returned to the incubator for another 8–10 days. At the end of this time the larger erythroid colonies (from primitive BFU-E), all granulopoietic colonies (from CFU-GM), and colonies containing multiple lineages of cells (from CFU-GEMM), were most readily distinguished and accurately counted in the same dish.

The preparation exhibited a 5–10 fold stimulation of DNA synthesis in short term (3 days) and long term proliferation assays. This ≈23 kDa fraction also enhanced the numbers of CFU-GEMM, CFU-GM, and BFU-E progenitor cells in the methylcellulose-based assays of bone marrow and cord blood cells as described above. When cord blood-derived CD34+ cells were treated with the fraction, a five-fold expansion of cells bearing the CD34+/CD38– phenotype was observed over a 12-day period.

Protein spots were also cut from a 2-D gel of the material eluted from the Mono S column with 50 mM NaCl and 100 mM NaCl and analyzed for bioactivity using a standard colony forming assay with PDL-1 (CD34+) cells stimulated with each of the fractions. Alternatively, bioactivity can be determined by tritiated thymidine uptake or by a colormetric assay, as described above using freshly isolated 34+ or other available CD34+ cells known to those of skill in the art. Bioactivity was determined for SAM.1 reactive spots identified from the peak eluted with 50 mM and for spots identified from the peak eluted with 100 mM. Only the major spots in the 100 mM fraction were isolated and found to be positive by the PDL-1 bioactivity assay. These proteins were sequenced and several were found to be a lipid binding protein.

About thirteen spots that resolved in the molecular weight range expected for SCPF from the 50 mM fraction (FIG. 21) were also isolated and tested for bioactivity. A western blot of the gel indicated that several spots interacted with SAM.1 antibody. A companion gel was electroblotted to PVDF and stained with Coomassie blue (see for example, Coligan, et al., 1992, supra, Unit 8.10, incorporated by reference). Spot 9 was antibody positive and was cut from the accompanying PVDF blot. Spot 9 was also found to be bioactive, however, sequence analysis was unable to be performed as the protein was blocked on the N-terminus. The sequence of the protein in Spot 9 can now be determined by routine methods such as enzymatic fragmentation and peptide sequence analysis by standard methods commonly used when proteins are blocked. Such methods are well known to those of skill in the art. Spot 8 was not reactive with SAM.1 antibody, however, it was bioactive in the PDL-1 assay. Sequence analysis of Spot 8 revealed that it was manganese (Mn) superoxide dismutase.

The pIs of the relevant SCPF spots, as determined by 2-D gel electrophoresis, are noted in FIG. 20. The pIs were determined from a 2-D gel after the sample was denatured in urea. (This is different from the native state of a protein when analyzed by IEF, where the protein is not denatured in urea). The thirteen spots had pIs ranging from about 6.2 to 7.8 and MW in the 23–27 kDa range.

8.5 Reactivity of SCPF with Antibody Against Various Cytokines

Western blot analyses were performed in order to determine whether SCPF was a previously identified cytokine or whether it was a novel protein. Table 12 shows the results of reactivity of anti-SAM.1, –hIL-3, –hIL-11, –hGM-CSF, –hSCF, –hIL-1a, –hIL-β, and –hG-CSF with themselves (as a positive control) and with SCPF. None of the antibodies other than SAM.1 reacted with SCPF.

TABLE 12

WESTERN BLOT ANALYSIS OF SCPF REACTIVITY WITH ANTI-CYTOKINE ANTIBODIES

| | Antibodies | | | | | | | | |
|---|---|---|---|---|---|---|---|---|---|
| | SAM.1 | hIL-3 | hIL-6 | hIL-11 | hGM-CFS | hSCF | hIL-1a | hIL-1β | hG-CSF |
| Cytokines | | | | | | | | | |
| rhIL-3 | – | + | / | / | / | / | / | / | / |
| rhIL-6 | – | / | + | / | / | / | / | / | / |
| rhIL-11 | – | / | / | + | / | / | / | / | / |
| rhSCF | – | / | / | / | + | / | / | / | / |
| rhGM-CSF | – | / | / | / | / | + | / | / | / |
| rhIL-1a | – | / | / | / | / | / | + | / | / |
| rhIL-1β | – | / | / | / | / | / | / | + | / |
| rhG-CSF | – | / | / | / | / | / | / | / | + |
| SCPF | + | – | – | – | – | – | – | – | – |

+ = positive reactivity
– = negative reactivity
/ = not tested

9. DEPOSIT OF CELL LINES

The 751 cell line and the ML-1 cell line have been deposited with the American Type Culture Collection, Rockville, Md., and have the following accession number:

| Cell Line | Accession No. |
|---|---|
| 75-1NA-15 | CRL 10992 |
| 751-NA-15 | CRL 12160 |
| ML-1 | CRL 11451 |

The present invention is not to be limited in scope by the specific embodiments described which are intended as single illustrations of individual aspects of the invention, and any cell lines, DNA constructs or factors which are functionally equivalent are within the scope this invention. Indeed, various modifications of the invention in addition to those shown and described herein will become apparent to those skilled in the art from the foregoing description and accompanying drawings. Such modifications are intended to fall within the scope of the appended claims.

---

What is claimed is:

1. A cell line having ATCC accession number CRL 12160.

2. A cell line having ATCC accession number CRL 11451.

3. A method for producing a stem cell proliferation factor, comprising: culturing cells from the cell line 751-NA-15 (ATCC accession number CRL 12160) under conditions that allow for expression of an isolatable polypeptide having the following properties:

(a) a molecular weight of about 32 kDa on SDS-PAGE when isolated as a secreted polypeptide;

(b) a molecular weight of about 37 kDa on SDS-PAGE when isolated from cell membrane fractions;

(c) isoforms having isoelectric points ranging from 7.0–8.0 as determined by 2-dimensional electrophoresis in the presence of urea;

(d) binds to $CD34^+$ human bone marrow cells in the presence of an antibody that binds to human CD34;

(e) induces proliferation of human bone marrow stem cells; and (f) induces proliferation of human bone marrow stem cells in the presence of an antibody that binds to and neutralizes IL-3, GM-CSF G-CSF or M-CSF.

4. A method for producing a stem cell proliferation factor, comprising culturing cells from cell line ML-1 (ATCC accession number CRL 11451) under conditions that allow for expression of an isolatable polypeptide having the following characteristics;

(a) a molecular weight of about 23 kDa as determined by 2-dimensional gel electrophoresis in the presence of urea;

(b) a molecular weight of about 27 kDa as determined by 1-dimensional SDS-PAGE;

(c) an isoelectric point of about 7.7 as determined by 2-dimensional gel electrophoresis in the presence of urea;

(d) an isoelectric point of about 9 as determined by flatbed gel electrophoresis in the absence of urea;

(e) stimulatory for proliferation of human blast cells in clonal assay;

(f) lacks binding to DEAE-cellulose and CM-cellulose; and (g) binds to MonoS.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

Lys Asp Arg Gly Pro Ala Gly Ala Leu
    1                   5